(12) United States Patent
Garneau-Tsodikova et al.

(10) Patent No.: US 11,535,592 B2
(45) Date of Patent: Dec. 27, 2022

(54) ANTIMICROBIAL COMPOUNDS, COMPOSITIONS, AND METHOD

(71) Applicant: University of Kentucky Research Foundation, Lexington, KY (US)

(72) Inventors: Sylvie Garneau-Tsodikova, Lexington, KY (US); Octavio Alberto Gonzalez, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 151 days.

(21) Appl. No.: 16/895,985

(22) Filed: Jun. 8, 2020

(65) Prior Publication Data
US 2020/0385348 A1 Dec. 10, 2020

Related U.S. Application Data

(60) Provisional application No. 62/858,753, filed on Jun. 7, 2019.

(51) Int. Cl.
*C07D 209/18* (2006.01)
*A61P 31/04* (2006.01)

(52) U.S. Cl.
CPC ............ *C07D 209/18* (2013.01); *A61P 31/04* (2018.01)

(58) Field of Classification Search
CPC .............................. C07D 209/18; A61P 31/04
See application file for complete search history.

(56) References Cited

FOREIGN PATENT DOCUMENTS

| WO | WO-2013055674 A1 * | 4/2013 | ............ A61K 31/404 |
| WO | WO-2015079254 A1 * | 6/2015 | ............ A61K 31/381 |

OTHER PUBLICATIONS

Gerits; FEMS Microbiol. Lett., 2017, 364, fnx005. DOI: 10.1093/femsle/fnx005. (Year: 2017).*
Martinez; European Journal of Medicinal Chemistry 2018, 157, 1202-1213. https://doi.org/10.1016/j.ejmech.2018.08.077 (Year: 2018).*
Srinivas; Organic Process Research & Development 2004, 8, 952-954. https://doi.org/10.1021/op049869i (Year: 2004).*
Howard, K. C., Gonzalez, O. A., & Garneau-Tsodikova, S.* (2020). Second generation of zafirlukast derivatives with improved activity against the oral pathogen Porphyromonas gingivalis. ACS Med Chem Lett., 11(10), 1905-1912.
Thamban Chandrika, N., Fosso, M. Y., Alimova, Y., May, A., Gonzalez, O. A.,* & Garneau-Tsodikova, S.* (2019). Novel zafirlukast derivatives exhibit selective antibacterial activity against Porphyromonas gingivalis. MedChemComm, 10(6), 926-933.

* cited by examiner

*Primary Examiner* — Daniel R Carcanague
(74) *Attorney, Agent, or Firm* — Stites & Harbison, PLLC; Mandy Wilson Decker

(57) ABSTRACT

The presently-disclosed subject matter generally relates to antimicrobial compounds, compositions, methods of making and methods of use thereof. The presently-disclosed subject matter further relates to compounds, compositions and methods for the control of *Porphyromonas gingivalis*.

21 Claims, 7 Drawing Sheets

ANTIMICROBIAL COMPOUNDS, COMPOSITIONS, AND METHOD

RELATED APPLICATIONS

This application claims priority from U.S. Provisional Patent Application No. 62/858,753 filed on Jun. 7, 2019 the entire disclosure of which is incorporated herein by this reference

TECHNICAL FIELD

The presently-disclosed subject matter relates to antimicrobial compounds, compositions, methods of making, and methods of use thereof. The presently-disclosed subject matter also relates to antimicrobial control of *Porphyromonas gingivalis*. The presently-disclosed subject matter further relates to treatment of periodontal disease.

BACKGROUND

Periodontal disease is a chronic inflammatory disease that is triggered by oral pathogenic bacteria (e.g., *Porphyromonas gingivalis*) and leads to tooth loss if untreated. This disease affects half of adult population in the United States and its prevalence significantly increases with aging.[1, 2] In addition to the oral local sequelae, periodontal disease has also been associated as a risk factor for diabetes, cardiovascular diseases, stroke, as well as arthritis.[3-5] *P. gingivalis* is a Gram-negative bacterium that is associated with periodontal disease.[6-9] Evidence indicates that *P. gingivalis* can invade oral epithelial cells and modulate innate responses that lead to oral dysbiosis and unresolved chronic inflammation.[10-13]

Although it has been suggested that local and systemic antibiotics can be used as adjunctive therapy for controlling periodontal disease,[14-16] there are no clear understanding and/or guidelines when it comes to selecting an antibiotic regimen for targeting specific periodontopathogens, without perturbing the normal oral commensal bacteria.[17, 18] This pitfall can result in poor efficacy against the targeted pathogens, which can be either resistant or poorly susceptible against the antibiotic(s) selected.[19]

In addition, the extensive use of antibiotics can result in development of drug-resistant bacteria, which can impact the effectiveness of the treatment. Thus, it is paramount that development of novel antibacterial agents for the treatment of periodontal disease become a priority.

Zafirlukast is an FDA-approved drug used for the effective inhibition of airway inflammation in the case of asthma treatment.[28, 29] Recently published work emphasized the use of zafirlukast as a treatment option for *Mycobacterium tuberculosis* and West Nile virus infections.[30, 31] The antibacterial activity of the zafirlukast against two oral pathogens, *P. gingivalis* and *Streptococcus* mutants, was also reported in recent literature.[32]

In the instant invention, chemically modified zafirlukast provided better agents for treating oral infections compared to this parent drug scaffold (FIG. 1). In zafirlukast, both a cyclopentyl carbamate attached to an N-methylindole and an arylsulfonamide scaffold are linked via a decorated benzoyl ring, which offers a unique opportunity for structure-activity relationship (SAR) studies. Herein, the synthesis of multiple zafirlukast derivatives is reported, where modifications on the indole (e.g., removal or replacement of the cyclopentyl carbamate by a nitro group, and removal of the methyl group from the indole amine), the arylsulfonamide (e.g., removal of the methyl substituent), as well as the benzoyl ring (e.g., change in its substituents and their substitution patterns) were made. The antibacterial activity of these zafirlukast derivatives against *P. gingivalis* and various other oral bacteria is also disclosed herein. In addition, the cytotoxic effect of these zafirlukast derivatives against human oral epithelial cells is disclosed herein.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

SUMMARY

Figure 1:
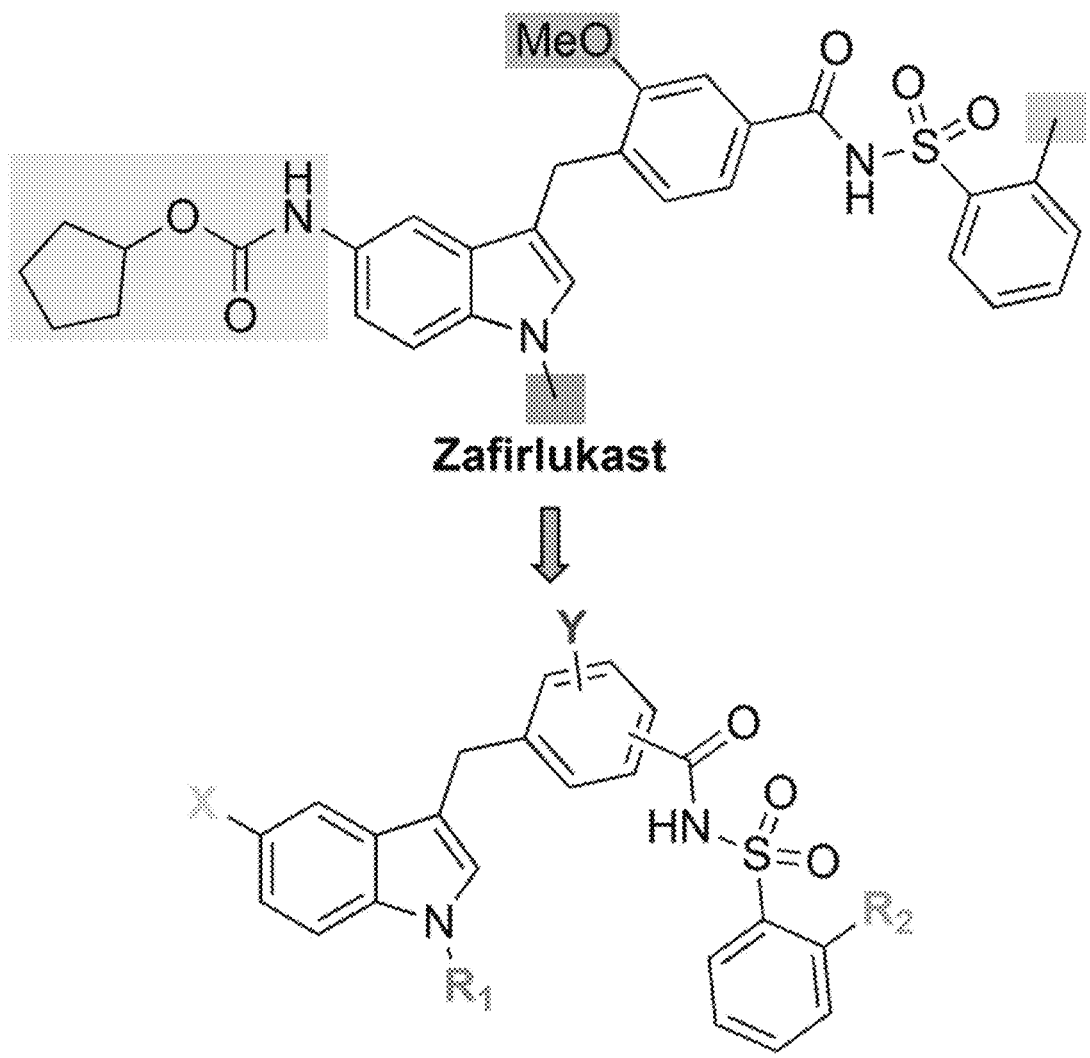
FIG. 1. Chemical structure of zafirlukast and exemplary derivatives in accordance with the presently-disclosed subject matter.

In accordance with the purpose(s) of the invention, as embodied and broadly described herein, the invention, in one aspect, relates to compounds useful as antimicrobial and bactericidal against *P. gingivalis*, methods of making said compounds, and methods of treating disorders associated with *P. gingivalis*, for example periodontal disease, using the same. Further disclosed are methods and compositions useful for treating a disease related to *P. gingivalis*. infection.

The presently-disclosed subject matter includes a compound having the formula (I) or a pharmaceutically acceptable salt thereof:

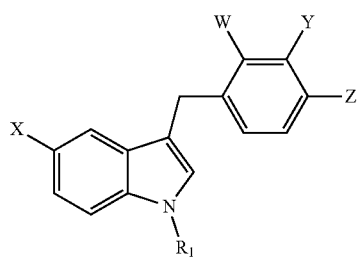

(I)

wherein,
$R_1$ is H or lower alkyl;
W, Y, and Z are independently selected from H,

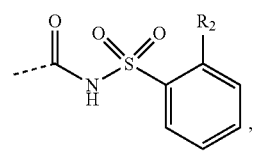

and $OR_3$, so long as only one of W, Y, and Z is

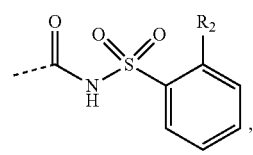

and $R_2$ and $R_3$ are each independently selected from H or lower alkyl; and
X is H, $NO_2$, $NR_4$, or $SO_2R_5$ where $R_4$ is H or lower alkyl, and $R_5$ is H or lower alkyl.

Some embodiments of the compound disclosed herein are selected from formulas (III, IV, or V) or a pharmaceutically acceptable salt thereof:

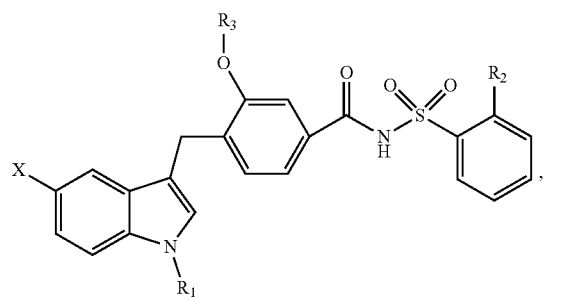

(III)

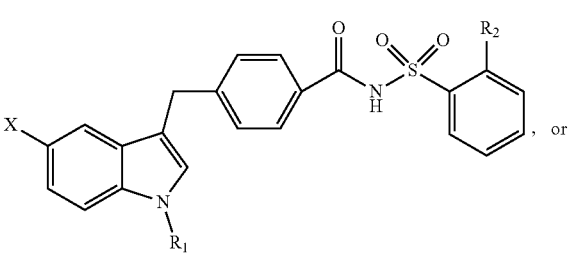

(IV)

, or

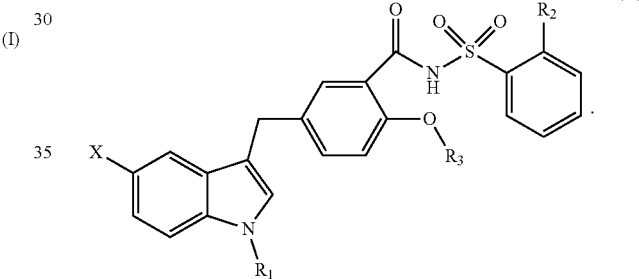

(V)

.

In embodiments of the compound disclosed herein, $R_1$, $R_2$, and $R_3$ are each independently H or methyl; and X is H or $NO_2$.

A "lower alkyl" group is an alkyl group containing one, two, three, four, five, or six carbon atoms.

In some embodiments of the presently-disclosed subject matter, $R_3$ is methyl.

In other embodiments of the presently disclosed subject matter the compound has the following formula (V):

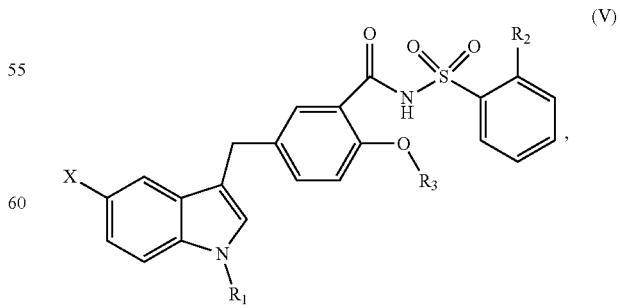

(V)

, wherein $R_1$ and $R_2$ are each independently H or methyl; $R_3$ is methyl; and X is H or $NO_2$.

In some embodiments the compound of the presently disclosed subject matter is selected from formulas (IV, VI, VII, VIII, IX, X, XI, XII, XIII, XIV, XV, or XVI) or a pharmaceutically acceptable salt thereof:
(IV)
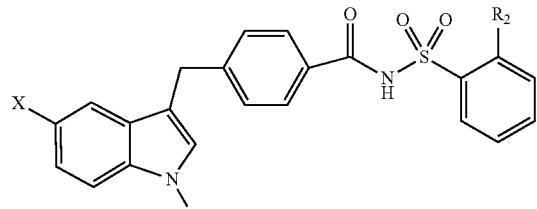
(VI)
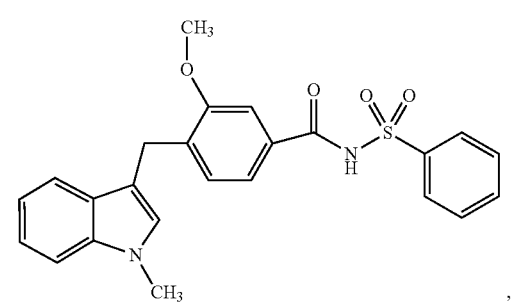
(VII)
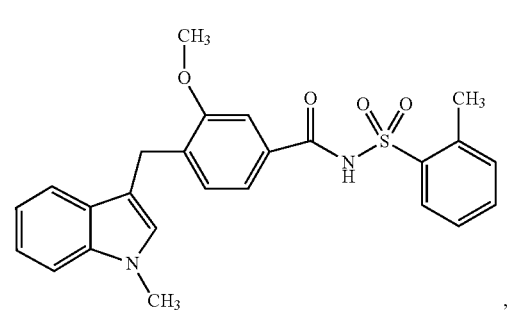
(VIII)
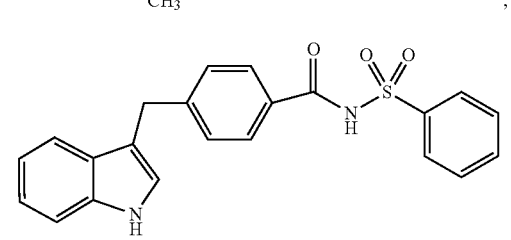
(IX)
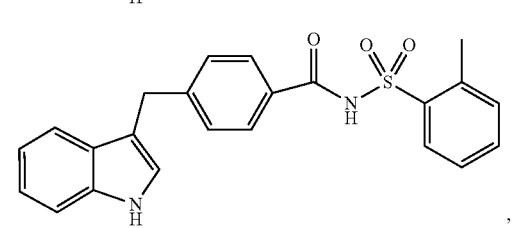
(X)
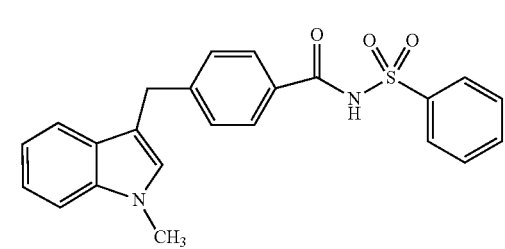
(XI)
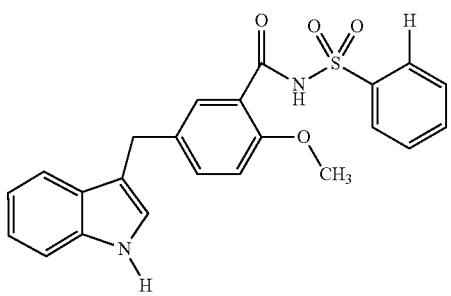
(XII)
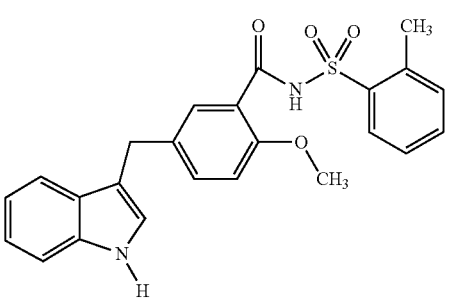
(XIII)
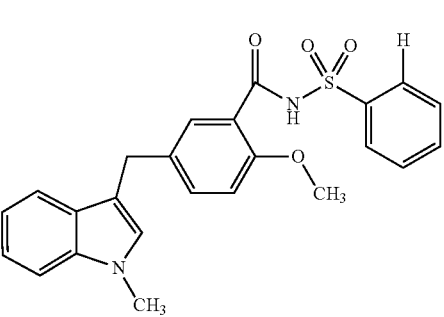
(XIV)
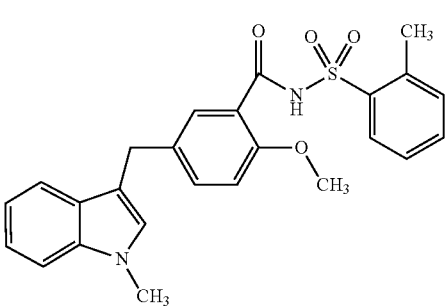
(XV)
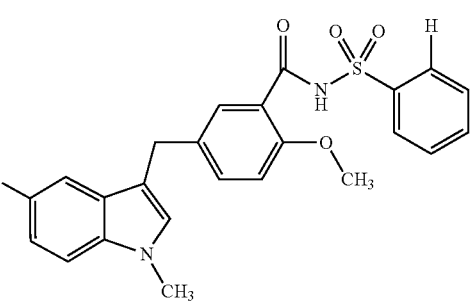
, and (XVI)

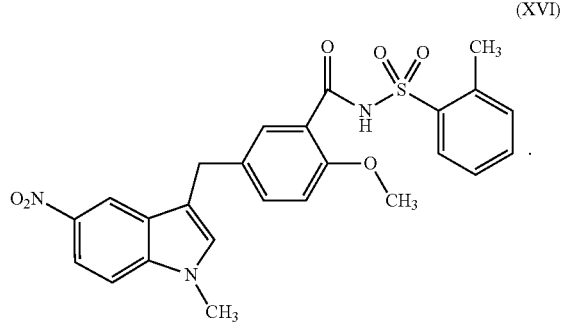

Some embodiments of the presently disclosed subject matter is a pharmaceutical composition comprising a compound disclosed herein, and a pharmaceutically-acceptable carrier.

Other embodiments are a method of controlling a microbe, comprising: contacting the microbe with an effective amount of a compound disclosed herein. In further embodiments of the method the microbe is *Porphyromonas* bacteria. In other embodiments, the bacteria is *P. gingivalis*. In further embodiments, the effective amount is between about 1 uM to about 100 uM.

Other embodiments of the presently disclosed subject matter include a method of treating a microbial infection, comprising: administering to a subject in need thereof an effective amount of a composition disclosed herein. In further embodiments of the method the microbe is *Porphyromonas* bacteria. In other embodiments, the bacteria is *P. gingivalis*. In further embodiments, the effective amount is between about 1 uM to about 100 uM. In some embodiments, the microbial infection caused periodontal disease in the subject. In other embodiments, a composition disclosed herein is administered prophylactically. In some embodiments, the subject is identified as being at risk of infection. In some embodiments, the method includes a composition selected from formulas (III, IV, or V) or a pharmaceutically acceptable salt thereof:

(III)

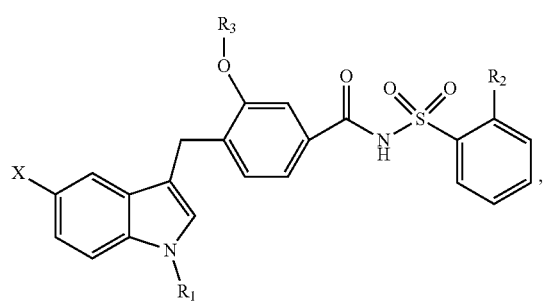

(IV)

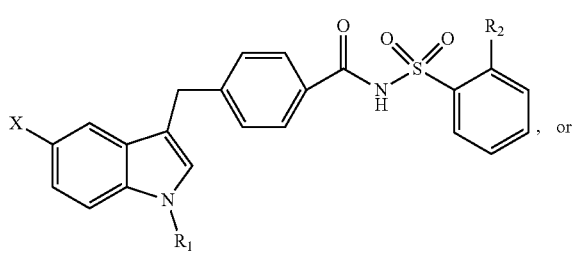

In other embodiments of the method, a composition of a compound disclosed herein is selected from formulas (IV, VI VII, VIII, IX, X, XI, XII, XIII, XIV, XV, or XVI) or a pharmaceutically acceptable salt thereof:

(IV)

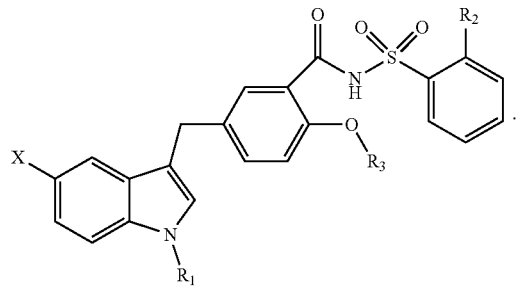

, (VI)

(VII)

(VIII)

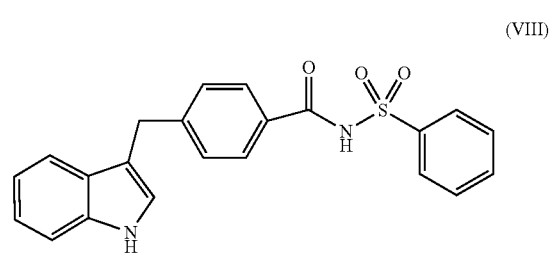

,

The presently-disclosed subject matter further includes a pharmaceutical composition that includes a compound as disclosed herein. In some embodiments, the composition includes at least two of the compounds as disclosed herein. In some embodiments, the composition includes at least one compound as disclosed herein and a second active agent useful for treating periodontal disease. In some embodiments, the composition includes a pharmaceutically-acceptable carrier.

The presently-disclosed subject matter further includes a method of controlling a microbe, which involves contacting the microbe with an effective amount of a compound or composition as disclosed herein.

The presently-disclosed subject matter further includes a method of treating a microbial infection, which involves administering to a subject in need thereof an effective amount of a compound or composition as disclosed herein. The administration can be, for example, by oral administration for systemic delivery, or topical administration. In this regard, in some embodiments, the composition is provided in a tablet or other suitable form for oral administration. In some embodiments, the composition is provided for topical administration. As will be appreciated by the skilled artisan, such topical administration can be to the oral cavity and provided, e.g., in a mouthwash, gel, etc. for such delivery.

In some embodiments of the methods disclosed herein, the microbe is an oral pathogen. In some embodiments, the microbe is involved in periodontal disease.

In some embodiments, the microbe is a bacteria. In some embodiments, the bacteria is *Porphyromonas*. In some embodiments, the bacteria is *P. gingivalis*.

In some embodiments, the microbe is a multidrug-resistant strain of a bacteria.

In some embodiments of the methods disclosed herein, the subject is identified as being at risk of infection.

In some embodiments of the methods disclosed herein, the compound or composition is administered before the microbe is present or before the microbial infection occurs in the subject. In some embodiments of the methods disclosed herein, the compound or composition is administered after the microbe is present or after the microbial infection occurs in the subject.

In this regard, as used herein, the terms "treatment" or "treating" relate to any treatment of a microbial infection, including but not limited to prophylactic treatment to prevent development or reduce severity of the infection. The terms "treatment" or "treating" include: (1) preventing an infection from occurring; (2) inhibiting an infection, i.e., arresting their development; (3) ameliorating or relieving the symptoms of infection, i.e., causing regression of the infection; (4) controlling, reducing, or eliminating a microbe associated with the infection; and (5) curing and/or eliminating the infection. As will be appreciated by the skilled artisan, elimination and/or prevention does not require 100% elimination and/or prevention of any and all microbes.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

In some aspects of the disclosed methods, the subject has been diagnosed with a need for treatment of a disease state associated with *Porphyromonas gingivalis* infection. In some aspects of the disclosed method, the subject has been diagnosed with a need for inhibition of *Porphyromonas gingivalis*.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibiting the growth of *Porphyromonas gingivalis*" means having been subjected to a physical examination by a person of skill, for example, a physician, and found to have a condition that can be diagnosed or treated by a compound or composition that can favorably inhibiting the growth of *Porphyromonas gingivalis*. Such a diagnosis can be in reference to a disorder, such as gingivitis, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and A, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by a formula $A^1OA^2$, where A and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by a formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by a formula —OH.

The term "ketone" as used herein is represented by a formula $A^1C(O)A^2$, where A and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "silyl" as used herein is represented by a formula —Si$A^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by a formulas —S(O)$A^1$, —S(O)$_2A^1$, —OS(O)$_2A^1$, or —OS(O)$_2$O$A^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by a formula —S(O)$_2A^1$, where A can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by a formula $A^1$S(O)$_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by a formula $A^1$S(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by a formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Additionally, unless expressly described as "unsubstituted", all substituents can be substituted or unsubstituted.

In some aspects, a structure of a compound can be represented by a formula:

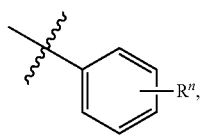

which is understood to be equivalent to a formula:

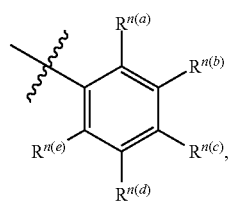

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

The following abbreviations are used herein. DMF: dimethyl formamide. DMSO: dimethylsulfoxide. MeOH: methanol. $CDCl_3$: Deuterated Chloroform. min: minute(s). EtOAc: ethyl acetate. EtOH: ethoanol. DMAP: 4-Dimethylaminopyridine. EDC: N-Ethyl-N'-(3-dimethylaminopropyl)carbodiimide. LCMS: liquid chromatography mass spectrometry. TFA: trifluoroacetic acid. MeCN: acetonitrile. $Et_3SiH$: Triethylsilane.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful inhibitors of the growth of *P. gingivalis*. It is also understood that the disclosed compounds can all be employed as corresponding pharmaceutical compositions.

In one aspect, the invention relates to compounds having a structure represented by the following formula:

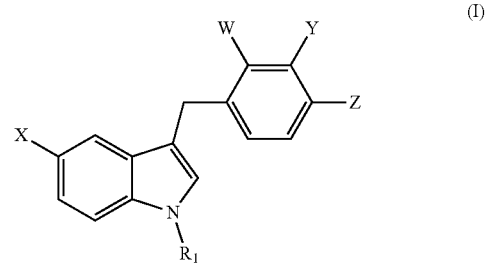

wherein,
$R_1$ is H or lower alkyl;
W, Y, and Z are independently selected from H,

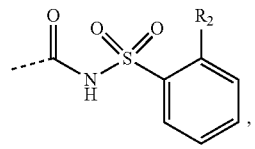

and $OR_3$, so long as only one of W, Y, and Z is

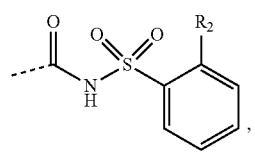

and $R_2$ and $R_3$ are each independently selected from H or lower alkyl; and
X is H, $NO_2$, $NR_4$, or $SO_2R_5$ where $R_4$ is H or lower alkyl, and $R_5$ is H or lower alkyl or a pharmaceutically acceptable salt thereof or a pharmaceutically acceptable derivative thereof.

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

An amount suitable for inhibiting the growth of *P. gingivalis* will generally be about 1 µM to about 100 µM.

It is understood, however, that the specific dose level for any particular subpatient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed compounds and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

In one aspect, the invention relates to a pharmaceutical composition comprising a compound disclosed herein or a pharmaceutically acceptable salt thereof or a pharmaceutically acceptable derivative thereof; and a pharmaceutically acceptable carrier.

In one aspect, the invention relates to pharmaceutical compositions comprising a compound having a structure represented by a compound of the following formula:

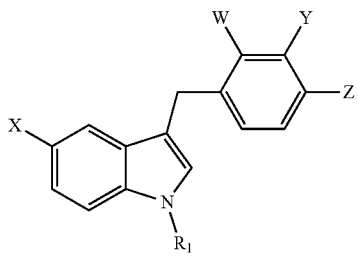

wherein,
R₁ is H or lower alkyl;
W, Y, and Z are independently selected from H,

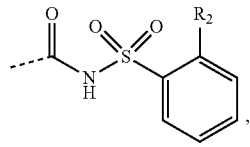

and OR₃, so long as only one of W, Y, and Z is

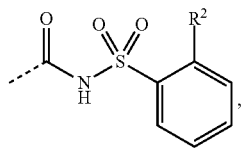

and R₂ and R₃ are each independently selected from H or lower alkyl; and
X is H, NO₂, NR₄, or SO₂R₅ where R₄ is H or lower alkyl, and R₅ is H or lower alkyl.

Examples

The presently-disclosed subject matter is further illustrated by the following specific but non-limiting examples. The following examples may include compilations of data that are representative of data gathered at various times during the course of development and experimentation related to the present invention.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

Materials and Instrumentations for Chemistry.

All chemicals were purchased from Sigma Aldrich (St. Louis, Mo.), Alfa Aesar (Ward Hill, Mass.), and AK scientific (Union City, Calif.), and used without further purification. Chemical reactions were monitored by thin layer chromatography (TLC) using Merck, Silica gel 60 F250 plates. Visualization was achieved using UV light and a ceric molybdate stain (5 g (NH₄)2Ce(NO₃)₆, 120 g (NH₄)₆Mo₇O₂₄·4H₂O, 80 mL H₂SO₄, 720 mL H2O). $^1$H and $^{13}$C NMR spectra were recorded at 400 and 100 MHz, respectively, on a Varian 400 MHz spectrometer, using the indicated deuterated solvents. Chemical shifts (d) are given in parts per million (ppm). Coupling constants (J) are given in Hertz (Hz), and conventional abbreviations used for signal shape are as follows: s=singlet; d=doublet; t=triplet; m=multiplet; dd=doublet of doublets; ddd=doublet of doublet of doublets; br s=broad singlet; dt=doublet of triplets. Liquid chromatography-mass spectrometry (LCMS) was carried out using an Agilent 1200 series Quaternary LC system equipped with a diode array detector, and Eclipse XDB-C18 column (250 mm×4.6 mm, 5 µm), and an Agilent 6120 Quadrupole MSD mass spectrometer (Agilent Technologies, Santa Clara, Calif.). LCMS [M+H]⁺ signals were consistent with the expected molecular weights for all of the reported compounds. Purity of the compound was further confirmed to be >95% by RP-HPLC by using one of the following methods: Method A: Flow rate=0.5 mL/min; λ=254 nm; column=Vydac 201SP™ C18, 250×4.6 mm, 90A 5 µm; eluents: A=H2O+0.1% TFA, B=MeCN; gradient profile: starting from 5% B, increasing from 5% to 100% B over 10 min, holding at 100% for 15 min, decreasing from 100% to 5% over 12 min. Prior to each injection, the HPLC column was equilibrated for 13 min with 5% B; Method B: Flow rate=0.5 mL/min; λ=254 nm; column=Vydac 201SP™ C18, 250×4.6 mm, 90A 5 µm; eluents: A=H₂O+0.1% TFA, B=MeCN; gradient profile: starting from 5% B, increasing from 5% to 100% B over 17 min, holding at 100% for 5 min, decreasing from 100% to 5% over 3 min. Prior to each injection, the HPLC column was equilibrated for 5 min with 5% B.

Synthesis of Compound 3.

A mixture of 1-methylindole (1.0 mL, 7.7 mmol), methyl

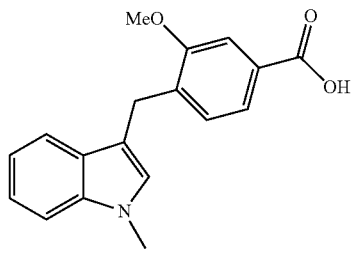 [SMILES: COc1cc(C(=O)O)ccc1Cc1cn(C)c2ccccc12]

4-(bromomethyl)-3-methoxybenzoate (1.0 g, 3.9 mmol), and Ag₂O H N (1.3 g, 5.8 mmol) in dioxane was stirred at 60° C. overnight. The reaction mixture was filtered through a bed of Celite®, and eluted with EtOAc. The filtrate was concentrated and purified by column chromatography (SiO₂ gel, pure Hexanes to Hexanes:EtOAc/9:1, Rf 0.26 in Hexanes:EtOAc/9:1) to afford the C-3 substituted indole. The latter was then dissolved in MeOH:THF:H₂O/5:1:1 (14 mL total), treated with KOH pellets (573 mg, 1.9 mmol) and stirred at room temperature overnight. After completion of the reaction, the organic solvents were removed in vacuo. The resulting mixture was diluted with H$_2$O, acidified to pH 1 with 1 N aqueous HCl, and extracted with CH$_2$C2 (3×). The combined organic layers were washed with brine, dried over MgSO$_4$, filtered, and concentrated. The crude product obtained was purified by column chromatography (SiO$_2$ gel, CH$_2$C2:MeOH/49:1, Rf 0.21 in CH$_2$C2:MeOH/19:1) to afford compound 3 (322 mg, 29%) as an off-white solid: $^1$H NMR (400 MHz, (CD$_3$)$_2$CO) δ 10.60 (very br s, 1H, CO$_2$H), 7.57 (d, J=1.6 Hz, 1H, aromatic), 7.52 (dd, J=8.0 Hz, J2=1.6 Hz, 1H, aromatic), 7.49 (d, J=8.0 Hz, 1H, aromatic), 7.32 (d, J=8.0 Hz, 1H, aromatic), 7.20 (d, J=8.0 Hz, 1H, aromatic), 7.13 (ddd, J=8.0 Hz, J2=7.2 Hz, J3=1.2 Hz, 1H, aromatic), 7.00 (s, 1H, aromatic), 6.98 (ddd, J=8.0 Hz, J2=7.2 Hz, J3=1.2 Hz, 1H, aromatic), 4.09 (s, 2H, CH$_2$Ar), 3.94 (s, 3H, OCH$_3$), 3.75 (s, 3H, NCH$_3$); $^{13}$C NMR (100 MHz, (CD$_3$)$_2$CO) δ 166.7, 157.2, 137.3, 135.5, 129.6, 129.5, 128.0, 127.6, 121.9, 121.2, 118.8, 118.5, 112.2, 110.9, 109.2, 55.0, 31.7, 24.8; m/z calcd for C$_{18}$H$_{17}$NO$_3$ 295.1; found 296.1 [M+H]$^+$.

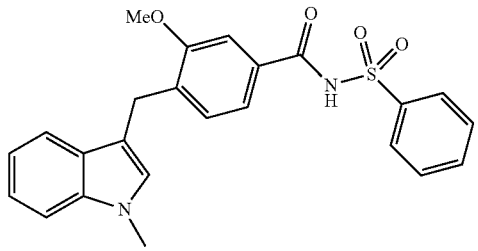 [SMILES: COc1cc(C(=O)NS(=O)(=O)c2ccccc2)ccc1Cc1cn(C)c2ccccc12]

Synthesis of Compound 4a.

A mixture of compound 3 (100 mg, 0.34 mmol), benzenesulfonamide (59 mg, 0.37 mmol), EDC.HCl (84 mg, 0.44 mmol), and DMAP (62 mg, 0.51 mmol) in anhydrous CH$_2$C2 (10 mL) was stirred at room temperature overnight. After completion of the reaction, the solvents were removed and the crude product obtained was purified by column chromatography (SiO$_2$ gel, pure Hexanes to Hexanes:EtOAc/1:1, Rf 0.50 in CH$_2$C2:MeOH/19:1) to afford compound 4a (124 mg, 84%) as an off-white solid: $^1$H NMR (400 MHz, (CD$_3$)$_2$CO) δ 10.85 (s, 1H, O=CNH), 8.08 (d, J=8.4 Hz, 2H, aromatic), 7.70 (t, J=7.6 Hz, 1H, aromatic), 7.61 (t, J=7.6 Hz, 2H, aromatic), 7.48 (s, 1H, aromatic), 7.44 (d, J=8.8 Hz, 1H, aromatic), 7.41 (d, J=9.2 Hz, 1H, aromatic), 7.32 (d, J=7.6 Hz, 1H, aromatic), 7.17 (d, J=7.6 Hz, 1H, aromatic), 7.12 (t, J=8.4 Hz, 1H, aromatic), 6.99 (s, 1H, aromatic), 6.96 (t, J=7.6 Hz, 1H, aromatic), 4.06 (s, 2H, CH$_2$Ar), 3.92 (s, 3H, OCH$_3$), 3.75 (s, 3H, NCH$_3$); $^{13}$C NMR (100 MHz, CDCl$_3$, FIG. S4) δ 164.2, 157.5, 138.4, 137.0, 136.6, 134.0, 129.9, 129.7, 129.2, 129.0, 128.5, 127.8, 127.4, 126.4, 121.6, 119.5, 119.1, 118.8, 112.0, 109.4, 109.2, 55.6, 32.6, 25.2; m/z calcd for C$_{24}$H$_{22}$N$_2$O$_4$S 434.1; found 435.1 [M+H]$^+$. Purity of the compound was further confirmed by RP-HPLC by using method B: Rt=24.93 min (95%).

Synthesis of Compound 4b.

A mixture of compound 3 (100 mg, 0.34 mmol), o-toluenesulfonamide (64 mg, 0.37 mmol), EDC.HCl (84 mg, 0.44 mmol), and DMAP (62 mg, 0.51 mmol) in anhydrous CH$_2$Cl$_2$ (10 mL) was stirred at room temperature overnight. After completion of the reaction, the solvents were removed and the crude product obtained was by

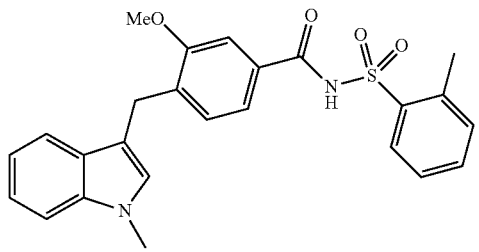 [SMILES: COc1cc(C(=O)NS(=O)(=O)c2ccccc2C)ccc1Cc1cn(C)c2ccccc12]

column chromatography (SiO$_2$ gel, pure Hexanes to Hexanes:EtOAc/1:1, Rf 0.47 in CH$_2$C2:MeOH/19:1) followed by recrystallization in EtOH to afford compound 4b (90 mg, 59%) as an off-white solid: 1H NMR (400 MHz, (CD$_3$)$_2$CO) δ 10.94 (s, 1H, O=CNH), 8.16 (dd, J1=8.0 Hz, J2=1.2 Hz, 1H, aromatic), 7.56 (td, J1=J2=7.6 Hz, J3=1.2 Hz, 1H, aromatic), 7.48 (s, 1H, aromatic), 7.49 (d, J=8.4 Hz, 1H, aromatic), 7.44 (td, J1=J2=7.6 Hz, J3=1.2 Hz, 1H, aromatic), 7.43 (dd, J1=8.0 Hz, J2=1.2 Hz, 1H, aromatic), 7.38 (d, J=7.6 Hz, 1H, aromatic), 7.32 (d, J=8.4 Hz, 1H, aromatic), 7.18 (d, J=7.6 Hz, 1H, aromatic), 7.12 (t, J=8.0 Hz, 1H, aromatic), 7.01 (s, 1H, aromatic), 6.97 (t, J=8.0 Hz, 1H, aromatic), 4.07 (s, 2H, CH$_2$Ar), 3.92 (s, 3H, OCH$_3$), 3.75 (s, 3H, NCH$_3$), 2.64 (s, 3H, ArCH$_3$); $^{13}$C NMR (100 MHz, (CD$_3$)$_2$CO) δ 164.4, 157.3, 137.9, 137.5, 136.0, 133.5, 132.3, 131.2, 130.6, 129.7, 127.9, 127.6, 127.3, 126.0, 121.2, 120.2, 118.7, 118.5, 112.0, 109.7, 109.2, 55.1, 31.7, 24.9, 19.4; m/z calcd for C$_{25}$H$_{24}$N$_2$O$_4$S 448.2; found 449.1 [M+H]$^+$. Purity of the compound was further confirmed by RP-HPLC by using method B: Rt=25.35 min (96%).

Synthesis of Compound 7.

A solution of indole (0.50 g, 4.3 mmol) and methyl 4-formylbenzoate

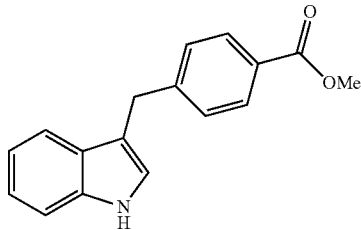 [SMILES: COC(=O)c1ccc(Cc2c[nH]c3ccccc23)cc1]

(0.70 g, 4.3 mmol) in anhydrous CH$_2$Cl$_2$ was cooled down to 0° C. in an ice-H$_2$O bath. Et$_3$SiH (2.0 mL, OMe 12.8 mmol) was then added, followed by TFA (0.65 mL, 8.5 mmol). The resulting mixture was stirred at 0° C. for 10 min before allowing it to warm up to room temperature overnight. The reaction was quenched with H$_2$O, and extracted with CH$_2$Cl$_2$ (3×). The combined organic layers were washed with NaHCO$_3$, H$_2$O, and brine, dried over MgSO$_4$, filtered, and concentrated. The crude product obtained was purified by column chromatography (SiO$_2$ gel, Hexanes:CH$_2$Cl$_2$/1:1, Rf 0.23 in Hexanes:CH$_2$Cl$_2$/1:2) to afford compound 7 (0.26 g, 23%) as an off-white solid: $^1$H NMR (400 MHz, CDCl$_3$) δ 8.05 (br s, 1H, NH), 7.95 (d, J=8.4 Hz, 2H, aromatic), 7.46 (d, J=7.6 Hz, 1H, aromatic), 7.35 (d, J=8.0 Hz, 1H, aromatic), 7.34 (d, J=8.4 Hz, 2H, aromatic), 7.19 (t, J=8.0 Hz, 1H, aromatic), 7.08 (t, J=7.6 Hz, 1H, aromatic), 6.92 (s, 1H, aromatic), 4.16 (s, 2H, CH$_2$Ar), 3.89 (s, 3H, ArCO$_2$CH$_3$); $^{13}$C NMR (100 MHz, CDCl$_3$) δ 167.3, 146.8, 136.4, 129.7 (2 carbons), 128.7 (2 carbons), 127.9, 127.2, 122.5, 122.2, 119.5, 119.0, 114.7, 111.2, 52.0, 31.7; m/z calcd for $C_{17}H_{15}NO_2$ 265.1; found 266.1 $[M+H]^+$.

Synthesis of Compound 8.

A solution of 1-methylindole (0.50 g, 3.8 mmol) and methyl 4-formylbenzoate (0.63 g, 3.8 mmol) in anhydrous $CH_2Cl_2$ was cooled down to 0° C. in

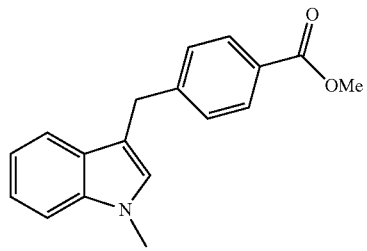 [SMILES: COC(=O)c1ccc(Cc2cn(C)c3ccccc23)cc1]

an ice-$H_2O$ bath. $Et_3SiH$ (1.8 mL, 11.4 mmol) was then added, followed by TFA (0.58 mL, 7.6 mmol). The resulting mixture was stirred at 0° C. for 10 min before allowing it to warm up to room temperature overnight. The reaction was quenched with $H_2O$, and extracted with $CH_2Cl_2$ (3×). The combined organic layers were washed with $NaHCO_3$, $H_2O$, and brine, dried over $MgSO_4$, filtered, and concentrated. The crude product obtained was purified by column chromatography ($SiO_2$ gel, Hexanes:$CH_2Cl_2$/1:1, Rf 0.35 in Hexanes:$CH_2C2$/1:1) to afford compound 8 (0.60 g, 56%) as an off-white solid: $^1$H NMR (400 MHz, $CDCl_3$) δ 7.95 (d, J=8.0 Hz, 2H, aromatic), 7.46 (d, J=7.6 Hz, 1H, aromatic), 7.35 (d, J=8.0 Hz, 2H, aromatic), 7.30 (d, J=8.4 Hz, 1H, aromatic), 7.22 (t, J=8.0 Hz, 1H, aromatic), 7.07 (t, J=8.0 Hz, 1H, aromatic), 6.77 (s, 1H, aromatic), 4.15 (s, 2H, $CH_2Ar$), 3.89 (s, 3H, $ArCO_2CH_3$), 3.73 (s, 3H, $NCH_3$); $^{13}$C NMR (100 MHz, $CDCl_3$) δ 167.2, 147.0, 137.2, 129.7 (2 carbons), 128.7 (2 carbons), 127.9, 127.6, 127.2, 121.7, 119.1, 118.9, 113.2, 109.2, 52.0, 32.6, 31.6; m z calcd for $C_{18}H_{17}NO_2$ 279.1; found 280.1 $[M+H]^+$.

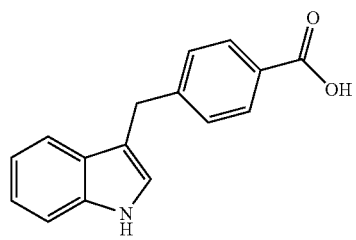 [SMILES: O=C(O)c1ccc(Cc2c[nH]c3ccccc23)cc1]

Synthesis of Compound 9.

A solution of compound 7 (186 mg, 0.63 mmol) in MeOH:THF:$H_2O$/5:1:1 (14 mL total) was treated with KOH pellets (247 mg, 4.4 mmol), and the mixture was stirred at room temperature overnight. After completion of the reaction, the organic solvents were removed in vacuo. The resulting mixture was diluted with $H_2O$, and acidified to pH 1 with 1 N aqueous HCl. The solid formed was filtered off, washed with $H_2O$, and air-dried to afford compound 9 (132 mg, 84%) as an off-white solid: $^1$H NMR (400 MHz, $(CD_3)_2CO$) δ 10.10 (br s, 1H, $CO_2H$), 7.93 (d, J=8.4 Hz, 2H, aromatic), 7.44 (d, J=7.6 Hz, 1H, aromatic), 7.42 (d, J=8.0 Hz, 2H, aromatic), 7.37 (d, J=8.4 Hz, 2H, aromatic), 7.17 (d, J=2.0 Hz, 1H, aromatic), 7.07 (t, J=8.4 Hz, 1H, aromatic), 6.95 (t, J=7.6 Hz, 1H, aromatic), 4.17 (s, 2H, $CH_2Ar$), 3.19 (very br s, 1H, NH); $^{13}$C NMR (100 MHz, $(CD_3)_2CO$) δ 166.8, 147.5, 137.0, 129.6 (2 carbons), 128.6 (2 carbons), 128.1, 127.4, 123.1, 121.3, 118.65, 118.59, 113.7, 111.3, 31.3; m/z calcd for $C_{16}H_{13}NO_2$ 251.1; found 250.2 $[M-H]^-$.

Synthesis of Compound 10.

A solution of compound 8 (200 mg, 0.71 mmol) in MeOH:THF:$H_2O$/5:1:1 (14 mL total) was treated with KOH pellets (254 mg, 6.4 mmol), and the

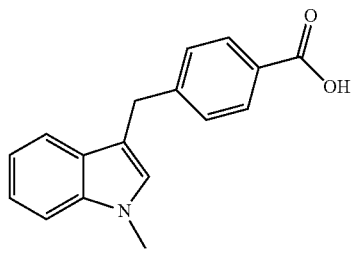 [SMILES: Cn1cc(Cc2ccc(C(=O)O)cc2)c2ccccc21]

mixture was stirred at room temperature overnight. After completion of the reaction, the organic solvents were OH removed in vacuo. The resulting mixture was diluted with $H_2O$, and acidified to pH 1 with 1 N aqueous HCl. The solid formed was filtered off, redissolved in $CH_2C2$ and purified by column chromatography ($SiO_2$ gel, $CH_2Cl_2$:MeOH/49:1, Rf 0.47 in $CH_2C2$:MeOH/19:1) to afford compound 10 (158 mg, 83%) as an off-white solid: $^1$H NMR (400 MHz, $(CD_3)_2CO$) δ 7.92 (d, J=8.0 Hz, 2H, aromatic), 7.44 (d, J=8.0 Hz, 1H, aromatic), 7.41 (d, J=8.0 Hz, 2H, aromatic), 7.33 (d, J=8.4 Hz, 1H, aromatic), 7.13 (t, J=8.0 Hz, 1H, aromatic), 7.04 (s, 1H, aromatic), 6.97 (t, J=8.0 Hz, 1H, aromatic), 4.15 (s, 2H, $CH_2Ar$), 3.77 (s, 3H, $NCH_3$); $^{13}$C NMR (100 MHz, $(CD_3)_2CO$) δ 166.8, 147.4, 137.4, 129.6 (2 carbons), 128.6 (2 carbons), 128.2, 127.7, 127.5, 121.3, 118.8, 118.5, 112.9, 109.3, 31.8, 31.1; m/z calcd for $C_{18}H_{17}NO_3$ 265.1; found 264.2 $[M-H]^-$.

Synthesis of Compound 11a.

A mixture of compound 9 (40 mg, 0.16 mmol),

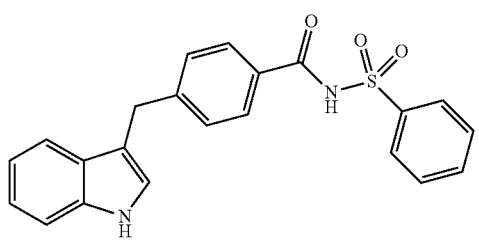 [SMILES: O=C(NS(=O)(=O)c1ccccc1)c1ccc(Cc2c[nH]c3ccccc23)cc1]

benzenesulfonamide (28 mg, 0.18 mmol), EDC.HCl (40 mg, 0.21 mmol), and DMAP (29 mg, 0.24 mmol) in anhydrous $CH_2Cl_2$ (5 mL) was stirred at room temperature overnight. Upon completion, the reaction mixture was purified by column chromatography ($SiO_2$ gel, $CH_2Cl_2$:MeOH/49:1, Rf 0.43 in $CH_2Cl_2$:MeOH/19:1) to afford compound 11a (36 mg, 58%) as an off-white solid: $^1$H NMR (400 MHz, $CDCl_3$) δ 8.70 (s, 1H, O=CNH), 8.13 (d, J=8.0 Hz, 2H, aromatic), 8.01 (s, 1H, NH), 7.64 (d, J=8.0 Hz, 2H, aromatic), 7.63 (t, J=7.6 Hz, 1H, aromatic), 7.53 (t, J=7.6 Hz, 2H, aromatic), 7.36 (t, J=8.0 Hz, 2H, aromatic), 7.32 (d, J=8.0 Hz, 2H, aromatic), 7.17 (t, J=7.6 Hz, 1H, aromatic), 7.04 (t, J=7.6 Hz, 1H, aromatic), 6.92 (s, 1H, aromatic), 4.13 (s, 2H, $CH_2Ar$); 13C NMR (100 MHz, $CDCl_3$) δ 164.2, 147.9, 138.4, 136.4, 134.0, 129.1 (2 carbons), 129.0 (2 carbons), 128.6, 128.5 (2 carbons), 127.9 (2 carbons), 127.1, 122.6, 122.2, 119.5, 118.8, 114.1, 111.3, 31.6; m/z calcd for C$_{22}$H$_{18}$N$_2$O$_3$S 390.1; found 391.1 [M+H]$^+$. Purity of the compound was further confirmed by RP-HPLC by using method A: Rt=19.67 min (97%).

Synthesis of Compound 11b.

A mixture of compound 9 (40 mg, 0.16 mmol), o-toluenesulfonamide (30 mg, 0.18 mmol EDC.HCl (40 mg, 0.21 mmol), and DMAP (29 mg,

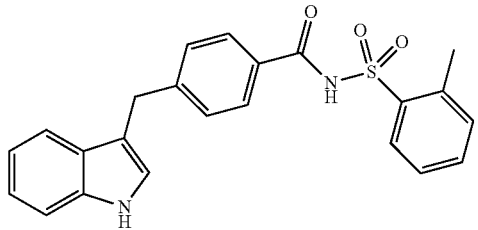 [SMILES: Cc1ccccc1S(=O)(=O)NC(=O)c1ccc(Cc2c[nH]c3ccccc23)cc1]

0.24 mmol) in anhydrous CH$_2$Cl$_2$ (5 mL) was stirred at room temperature overnight. Upon completion, the reaction mixture was purified by column chromatography (SiO$_2$ gel, CH$_2$Cl$_2$:MeOH/49:1, Rf 0.46 in CH$_2$Cl$_2$:MeOH/19:1) to afford compound 11b (67 mg, quant.) as an off-white solid: $^1$H NMR (400 MHz, CDCl$_3$) δ 9.36 (s, 1H, O=CNH), 8.24 (d, J=8.0 Hz, 1H, aromatic), 8.08 (s, 1H, NH), 7.67 (d, J=8.0 Hz, 2H, aromatic), 7.48 (t, J=7.6 Hz, 1H, aromatic), 7.38 (t, J=7.6 Hz, 2H, aromatic), 7.34 (d, J=7.6 Hz, 1H, aromatic), 7.30-7.24 (m, 3H, aromatic), 7.16 (t, J=7.6 Hz, 1H, aromatic), 7.04 (t, J=7.6 Hz, 1H, aromatic), 6.89 (s, 1H, aromatic), 4.10 (s, 2H, CH$_2$Ar), 2.66 (s, 3H, ArCH$_3$); $^{13}$C NMR (100 MHz, CDCl$_3$) δ 164.2, 147.8, 137.6, 136.5, 136.4, 134.0, 132.5, 131.5, 129.2 (2 carbons), 128.5, 128.0 (2 carbons), 127.1, 126.4, 122.6, 122.2, 119.5, 118.8, 114.1, 111.3, 31.6, 20.4; m/z calcd for C$_{23}$H$_{20}$N$_2$O$_3$S 404.1; found 403.1 [M−H]$^−$. Purity of the compound was further confirmed by RP-HPLC by using method B: Rt=23.58 min (97%).

Synthesis of Compound 12a.

A mixture of compound 10 (40 mg, 0.15 mmol),

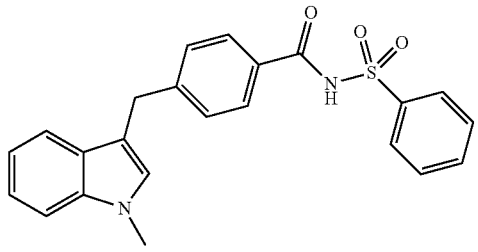 [SMILES: Cn1cc(Cc2ccc(C(=O)NS(=O)(=O)c3ccccc3)cc2)c2ccccc21]

benzenesulfonamide (23 mg, 0.15 mmol), EDC.HCl (34 mg, 0.18 mmol), and DMAP (25 mg, 0.20 mmol) in anhydrous CH$_2$Cl$_2$ (5 mL) was stirred at room temperature overnight. Upon completion, the reaction mixture was purified by column chromatography (SiO$_2$ gel, CH$_2$Cl$_2$:MeOH/49:1, Rf 0.51 in CH$_2$Cl$_2$:MeOH/19:1) to afford compound 12a (59 mg, 97%) as an off-white solid: $^1$H NMR (400 MHz, CDCl$_3$) δ 9.12 (s, 1H, O=CNH), 8.13 (d, J=8.0 Hz, 2H, aromatic), 7.67 (d, J=8.4 Hz, 2H, aromatic), 7.61 (t, J=7.2 Hz, 1H, aromatic), 7.51 (t, J=8.0 Hz, 2H, aromatic), 7.37 (d, J=8.0 Hz, 1H, aromatic), 7.30 (d, J=8.4 Hz, 2H, aromatic), 7.28 (d, J=8.4 Hz, 1H, aromatic), 7.20 (t, J=8.0 Hz, 1H, aromatic), 7.03 (t, J=7.2 Hz, 1H, aromatic), 6.74 (s, 1H, aromatic), 4.09 (s, 2H, CH$_2$Ar), 3.71 (s, 3H, NCH$_3$); $^{13}$C NMR (100 MHz, CDCl$_3$) δ 164.1, 148.0, 138.5, 137.1, 134.0, 129.2 (2 carbons), 129.0 (2 carbons), 128.61, 128.56 (2 carbons), 127.9 (2 carbons), 127.5, 127.3, 121.8, 119.0, 118.9, 112.6, 109.3, 32.6, 31.5; m/z calcd for C$_{23}$H$_{20}$N$_2$O$_3$S 404.1; found 405.1 [M+H]$^+$. Purity of the compound was further confirmed by RP-HPLC by using method A: Rt=25.00 min (99%).

Synthesis of Compound 13.

A solution of 5-nitro indole (1.0 g, 6.17 mmol) in

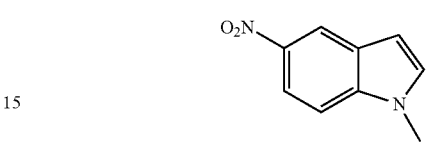

anhydrous DMF (20 mL) was treated with NaH (60% in mineral oil, 0.27 g, 6.78 mmol), and the mixture was stirred at room temperature for 1 h. Iodomethane (0.6 mL, 9.25 mmol) was then slowly added, and the resulting mixture was stirred at room temperature overnight. The reaction was quenched by pouring onto ice and extracted with CH$_2$Cl$_2$ (3×). The combined organic layers were washed with NaHCO$_3$, H$_2$O, and brine, dried over MgSO$_4$, filtered, and concentrated. The crude product obtained was triturated in hexanes and filtered to give the known compound 13$^1$ (0.78 g, 72%) as a yellow solid: $^1$H NMR (400 MHz, CDCl$_3$, which matches the lit.,$^1$) δ 8.57 (d, J=2.0 Hz, 1H, aromatic), 8.12 (dd, J1=9.2 Hz, J2=2.0 Hz, 1H, aromatic), 7.32 (d, J=8.8 Hz, 1H, aromatic), 7.19 (d, J=3.2 Hz, 1H, aromatic), 6.66 (d, J=2.4 Hz, 1H, aromatic), 3.85 (s, 3H, NCH$_3$).

Synthesis of Compound 15.

A solution of indole (0.30 g, 2.6 mmol) and methyl 5-formyl-2-methoxybenzoate

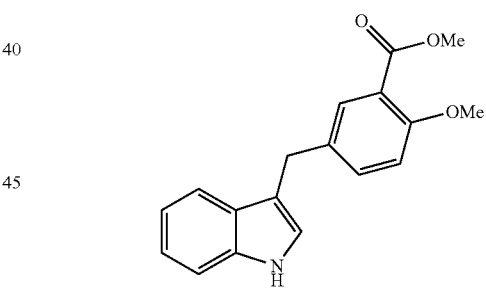

(0.50 g, 2.6 mmol) in anhydrous CH$_2$C2 was cooled down to 0° C. in an ice-H$_2$O bath. Et$_3$SiH (1.2 mL, 7.2 mmol) was then added, followed by TFA (0.4 mL, 5.1 mmol). The resulting mixture was stirred at 0° C. for 10 min before allowing it to warm up to room temperature overnight. The reaction was quenched with H$_2$O, and extracted with CH$_2$Cl$_2$ (3×). The combined organic layers were washed with NaHCO$_3$, H$_2$O, and brine, dried over MgSO$_4$, filtered, and concentrated. The crude product obtained was purified by column chromatography (SiO$_2$ gel, pure Hexanes to Hexanes:EtOAc/3:1, Rf 0.25 in Hexanes:EtOAc/3:1) to afford compound 15 (0.34 g, 43%) as a brown oil: $^1$H NMR (400 MHz, CDCl$_3$) δ 8.29 (s, 1H), 7.79 (d, J=2.4 Hz, 1H, aromatic), 7.51 (d, J=8.4 Hz, 1H, aromatic), 7.36 (dd, J1=8.0 Hz, J2=2.4 Hz, 1H, aromatic), 7.32 (d, J=7.6 Hz, 1H, aromatic), 7.19 (td, J1=8.0 Hz, J2=1.2 Hz, 1H, aromatic), 7.10 (td, J1=8.4 Hz, J2=1.2 Hz, 1H, aromatic), 6.86 (d, J=8.4

Hz, 1H, aromatic), 6.84 (s, 1H, aromatic), 4.08 (s, 2H, CH$_2$Ar), 3.89 (s, 3H, ArCO$_2$CH$_3$), 3.84 (s, 3H, ArOCH$_3$); $^{13}$C NMR (100 MHz, CDCl$_3$). δ 167.1, 157.5, 136.6, 133.8, 133.2, 131.7, 127.3, 122.6, 122.0, 119.6, 119.3, 119.0, 115.3, 112.2, 111.3, 56.1, 52.1, 30.6; m/z calcd for C$_{18}$H$_{17}$NO$_3$ 295.1; found 296.1 [M+H]$^+$.

Synthesis of Compound 16.

A solution of 1-methylindole (0.32 mL, 2.6 mmol) and

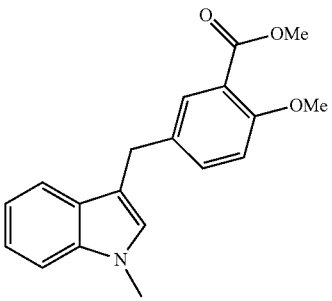 [SMILES: COC(=O)c1cc(Cc2cn(C)c3ccccc23)ccc1OC]

methyl 5-formyl-2-methoxybenzoate (0.50 g, 2.6 mmol) in anhydrous CH$_2$C2 was cooled down to 0° C. in an ice-H$_2$O bath. Et3SiH (1.2 mL, 7.2 mmol) was then added, followed by TFA (0.4 mL, 5.1 mmol). The resulting mixture was stirred at 0° C. for 10 min before allowing it to warm up to room temperature overnight. The reaction was quenched with H$_2$O, and extracted with CH$_2$Cl$_2$ (3×). The combined organic layers were washed with NaHCO$_3$, H$_2$O, and brine, dried over MgSO$_4$, filtered, and concentrated. The crude product obtained was purified by column chromatography (SiO$_2$ gel, pure Hexanes to Hexanes:EtOAc/3:1, Rf 0.36 in Hexanes:EtOAc/3:1) to afford compound 16 (0.71 g, 89%) as an off-white solid: $^1$H NMR (400 MHz, CDCl$_3$) δ 7.72 (d, J=2.4 Hz, 1H, aromatic), 7.47 (dt, J1=8.0 Hz, J2=1.2 Hz, 1H, aromatic), 7.34 (dd, J1=8.8 Hz, J2=2.4 Hz, 1H, aromatic), 7.27 (d, J=8.0 Hz, 1H, aromatic), 7.20 (td, J1=8.0 Hz, J2=0.8 Hz, 1H, aromatic), 7.05 (td, J1=8.0 Hz, J2=1.2 Hz, 1H, aromatic), 6.87 (d, J=8.8 Hz, 1H, aromatic), 6.72 (s, 1H, aromatic), 4.04 (s, 2H, CH$_2$Ar), 3.86 (s, 6H, ArCO$_2$CH$_3$, ArOCH$_3$), 3.72 (s, 3H, NCH$_3$); $^{13}$C NMR (100 MHz, CDCl$_3$) δ 166.9, 157.4, 137.2, 133.6, 133.2, 131.7, 127.6, 127.1, 121.6, 119.8, 119.1, 118.8, 114.1, 112.1, 109.2, 56.1, 52.0, 32.6, 30.5; m/z calcd for C$_{19}$H$_{19}$NO$_3$ 309.1; found 310.1 [M+H]$^+$.

Synthesis of Compound 17.

A solution of 5-nitroindole (1.00 g, 5.1 mmol) and methyl 5-formyl-2-methoxybenzoate (0.84 g, 5.1 mmol) in anhydrous CH$_2$Cl$_2$ was cooled down

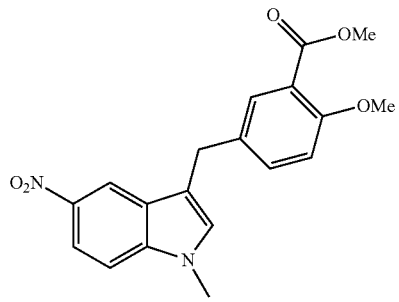 [SMILES: COC(=O)c1cc(Cc2cn(C)c3ccc([N+](=O)[O-])cc23)ccc1OC]

to 0° C. in an ice-H$_2$O bath. Et$_3$SiH (2.3 mL, 14.4 mmol) was then added, followed by TFA (0.8 mL, 10.3 mmol). The resulting mixture was stirred at 0° C. for 10 min before allowing it to warm up to room temperature overnight. The reaction was quenched with H$_2$O, and extracted with CH$_2$Cl$_2$ (3×). The combined organic layers were washed with NaHCO$_3$, H$_2$O, and brine, dried over MgSO$_4$, filtered, and concentrated. The crude product obtained was purified by column chromatography (SiO$_2$ gel, Hexanes:EtOAc/3:1 to Hexanes:EtOAc/1:1, Rf 0.32 in Hexanes:EtOAc/1:1) to afford the C-3 alkylated indole (0.50 g, 29%) as a yellow solid. A solution of this C-3 alkylated indole (250 mg, 0.73 mmol) in anhydrous DMF (10 mL) was treated with NaH (60% in mineral oil, 59 mg, 1.47 mmol), and the mixture was stirred at room temperature for 1 h. Iodomethane (0.07 mL, 1.10 mmol) was then added, and the resulting mixture was stirred at room temperature overnight. The reaction was quenched by pouring onto ice and extracted with CH$_2$Cl$_2$ (3×). The combined organic layers were washed with NaHCO$_3$, H$_2$O, and brine, dried over MgSO$_4$, filtered, and concentrated. The crude product obtained was purified by column chromatography (SiO$_2$ gel, Hexanes:EtOAc/2:1 to pure EtOAc, Rf 0.41 in Hexanes:EtOAc/1:1) to afford compound 17 (147 mg, 57%) as a yellow solid: $^1$H NMR (400 MHz, CDCl$_3$) δ 8.46 (d, J=2.0 Hz, 1H, aromatic), 8.10 (dd, J1=8.8 Hz, J2=2.4 Hz, 1H, aromatic), 7.68 (d, J=2.4 Hz, 1H, aromatic), 7.35 (dd, J1=8.4 Hz, J2=2.0 Hz, 1H, aromatic), 7.27 (d, J=8.8 Hz, 1H, aromatic), 6.91 (d, J=8.4 Hz, 1H, aromatic), 6.84 (s, 1H, aromatic), 4.05 (s, 2H, CH$_2$Ar), 3.87 (s, 3H, ArOCH$_3$), 3.85 (s, 3H, ArCO$_2$CH$_3$), 3.77 (s, 3H, NCH3); $^{13}$C NMR (100 MHz, CDCl$_3$) δ 166.8, 157.7, 141.2, 139.9, 133.5, 131.8, 131.7, 130.1, 126.9, 120.1, 117.5, 117.4, 116.5, 112.3, 109.1, 56.1, 52.0, 33.1, 30.1; m/z calcd for C$_{19}$H$_{18}$N$_2$O$_5$ 354.1; found 355.1 [M+H]$^+$.

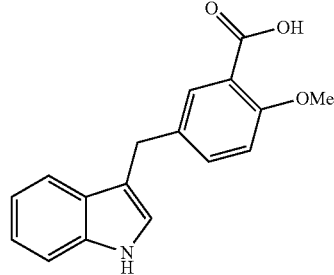 [SMILES: COc1ccc(Cc2c[nH]c3ccccc23)cc1C(=O)O]

Synthesis of Compound 18.

A solution of compound 15 (115 mg, 0.29 mmol) in MeOH/THF/H$_2$O (5 mL/1 mL/1 mL) was treated with KOH pellets (114 mg, 2.04 mmol), and the mixture was refluxed at 65° C. for 2 h. After completion of the reaction, the reaction mixture was concentrated to dryness to afford compound 18 (68 mg, 93%) as an N off-white solid: $^1$H NMR (400 MHz, CD$_3$OD) δ 8.52 (s, 1H), 7.37 (d, J=7.6 Hz, 1H, aromatic), 7.30 (d, J=2.4 Hz, 1H, aromatic), 7.27 (d, J=7.6 Hz, 1H, aromatic), 7.13 (dd, J1=8.4 Hz, J2=2.4 Hz, 1H, aromatic), 7.01 (t, J=7.6 Hz, 1H, aromatic), 6.94 (s, 1H, aromatic), 6.88 (t, J=7.6 Hz, 1H, aromatic), 6.83 (d, J=8.8 Hz, 1H, aromatic), 3.98 (s, 2H, CH$_2$Ar), 3.75 (s, 3H, ArOCH$_3$); $^{13}$C NMR (100 MHz, (CD$_3$)$_2$SO) δ 167.8, 156.7, 136.8, 133.8, 133.3, 130.8, 127.3, 123.6, 121.4, 121.3, 118.9, 118.7, 114.2, 112.8, 111.8, 56.2, 30.3; m/z calcd for C$_{17}$H$_{15}$NO$_3$ 281.1; found 282.1 [M+H]$^+$.

Synthesis of Compound 19.

A solution of compound 16 (250 mg, 0.81 mmol) in

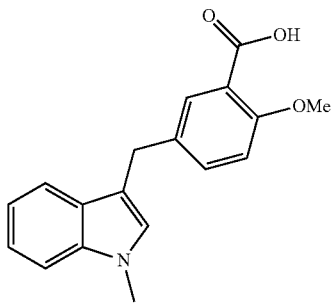 [SMILES: COc1ccc(Cc2cn(C)c3ccccc23)cc1C(=O)O]

MeOH/THF/H$_2$O (5 mL/1 mL/1 mL) was treated with KOH pellets (317 mg, 5.66 mmol), and the mixture was refluxed at 65° C. for 2 h. After completion of the reaction, the organic solvents were removed in vacuo. The resulting mixture was acidified to pH 1 with 1 N aqueous HCl and extracted with CH$_2$C2 (3×). The combined organic layers were washed with brine, dried over MgSO$_4$, filtered, and concentrated to afford compound 19 (223 mg, 93%) as an off-white solid: $^1$H NMR (400 MHz, CDCl$_3$) δ 8.13 (d, J=2.4 Hz, 1H, aromatic), 7.45-7.41 (m, 2H, aromatic), 7.27 (d, J=8.0 Hz, 1H, aromatic), 7.19 (td, J1=8.0 Hz, J2=1.2 Hz, 1H, aromatic), 7.04 (td, J1=8.0 Hz, J2=1.2 Hz, 1H, aromatic), 6.93 (d, J=8.4 Hz, 1H, aromatic), 6.79 (s, 1H, aromatic), 4.07 (s, 2H, CH$_2$Ar), 4.02 (s, 3H, ArOCH$_3$), 3.73 (s, 3H, NCH$_3$); $^{13}$C NMR (100 MHz, CDCl$_3$) δ 165.9, 156.5, 137.2, 135.6, 135.2, 133.5, 127.5, 127.2, 121.7, 119.0, 118.9, 117.2, 113.5, 111.8, 109.3, 56.7, 32.6, 30.5; m/z calcd for C$_{18}$H$_{16}$N$_2$O$_5$ 295.1; found 296.1 [M+H]$^+$.

Synthesis of Compound 20.

A solution of compound 17 (112 mg, 0.32 mmol) in

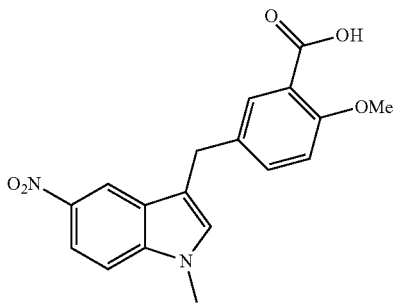 [SMILES: COc1ccc(Cc2cn(C)c3ccc([N+](=O)[O-])cc23)cc1C(=O)O]

MeOH/THF/H$_2$O (3 mL/1 mL/0.6 mL) was treated with KOH pellets (124 mg, 2.21 mmol), and the mixture was refluxed at 65° C. for 2 h. After completion of the reaction, the organic solvents were removed in vacuo. The resulting mixture was acidified to pH 1 with 1 N aqueous HCl. The precipitate was filtered and eluted with H$_2$O to afford compound 20 (94 mg, 87%) as a yellow solid: $^1$H NMR (400 MHz, CDCl$_3$) δ 10.7 (very br s, 1H, CO$_2$H), 8.38 (d, J=2.0 Hz, 1H, aromatic), 8.10 (dd, J1=8.8 Hz, J2=2.0 Hz, 1H, aromatic), 8.04 (d, J=2.4 Hz, 1H, aromatic), 7.49 (dd, J1=8.4 Hz, J2=2.0 Hz, 1H, aromatic), 7.28 (d, J=9.2 Hz, 1H, aromatic), 7.00 (d, J=8.0 Hz, 1H, aromatic), 6.94 (s, 1H, aromatic), 4.09 (s, 2H, CH$_2$Ar), 4.05 (s, 3H, ArOCH$_3$), 3.79 (s, 3H, NCH$_3$); $^{13}$C NMR (100 MHz, CDCl$_3$) δ 165.2, 156.5, 141.2, 140.0, 135.0, 134.4, 133.6, 130.3, 126.8, 117.6, 117.5, 116.5, 116.4, 111.9, 109.2, 56.8, 33.2, 30.1; m/z calcd for C$_{18}$H$_{16}$N$_2$O$_5$ 340.1; found 323.1 [M–OH]$^+$.

Synthesis of Compound 21a.

A mixture of compound 18 (30 mg, 0.11 mmol),

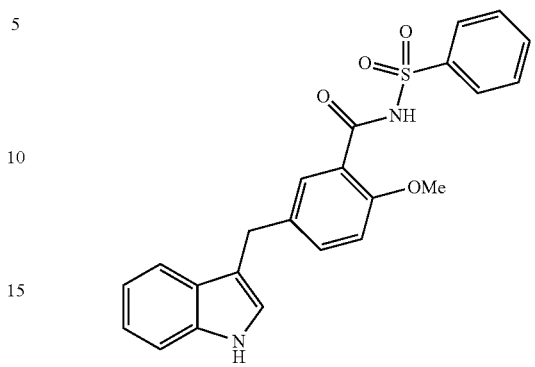

benzenesulfonamide (20 mg, 0.13 mmol), EDC.HCl (33 mg, 0.17 mmol), and DMAP (23 mg, 0.19 mmol) in anhydrous SCH$_2$Cl$_2$ (5 mL) was stirred at room temperature overnight. Upon completion, the reaction mixture was diluted with H$_2$O and extracted with CH$_2$Cl$_2$ (3×). The combined organic layers were washed with brine, dried over MgSO$_4$, filtered, and concentrated. The crude product obtained was purified by column chromatography (SiO$_2$ gel, pure CH$_2$Cl$_2$, Rf 0.26 in pure CH$_2$Cl$_2$) to afford compound 21a (9 mg, 20%) as an off-white solid: $^1$H NMR (400 MHz, CDCl$_3$) δ 10.51 (br s, 1H, NHSO$_2$), 10.02 (br s, 1H, NH), 8.08 (d, J=7.6 Hz, 2H, aromatic), 7.77 (s, 1H, aromatic), 7.69 (t, J=7.2 Hz, 1H, aromatic), 7.60 (t, J=7.2 Hz, 2H, aromatic), 7.50 (dd, J1=8.4 Hz, J2=2.4 Hz, 1H, aromatic), 7.38 (d, J=8.0 Hz, 1H, aromatic), 7.34 (d, J=8.4 Hz, 1H, aromatic), 7.12 (d, J=2.0 Hz, 1H, aromatic), 7.10 (s, 1H, aromatic), 7.04 (t, J=7.6 Hz, 1H, aromatic), 6.91 (t, J=7.6 Hz, 1H, aromatic), 4.05 (s, 2H, CH$_2$Ar), 4.02 (s, 3H, ArOCH$_3$); $^{13}$C NMR (100 MHz, (CD$_3$)$_2$CO) δ 162.5, 156.3, 139.7, 137.0, 135.1, 134.9, 133.6, 131.2, 128.8, 128.3, 127.3, 123.0, 122.8, 121.3, 119.0, 118.6, 118.5, 114.2, 112.2, 111.3, 111.2, 56.1, 30.0; m/z calcd for C$_{23}$H$_2$N$_2$O$_4$S 420.1; found 421.1 [M+H]$^+$. Purity of the compound was further confirmed by RP-HPLC by using method A: Rt=19.92 min (98%).

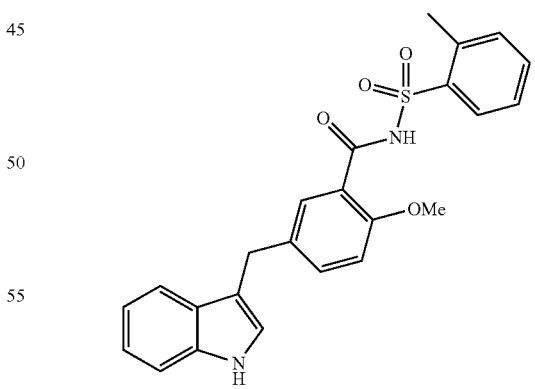

Synthesis of Compound 21b.

A mixture of compound 18 (50 mg, 0.18 mmol), o-toluenesulfonamide (33 mg, 0.20 mmol), EDC.HCl (44 mg, 0.23 mmol), and DMAP (33 mg, 0.27 mmol) in anhydrous CH$_2$Cl$_2$ (10 mL) was stirred at room temperature overnight. Upon completion, the reaction mixture was purified by column chromatography (SiO$_2$ gel, CH$_2$Cl$_2$:MeOH/49:1, Rf 0.50 in Hexanes:EtOAc/1:1) to afford compound 21b (73 mg, 95%) as an off-white solid: ¹H NMR (400 MHz, (CD₃)₂CO) δ 10.60 (s, 1H, NHSO₂), 10.01 (s, 1H, NH), 8.14 (dd, J1=8.0 Hz, J2=1.6 Hz, 1H, aromatic), 7.73 (d, J=2.0 Hz, 1H, aromatic), 7.54 (td, J1=8.0 Hz, J2=1.6 Hz, 1H, aromatic), 7.51 (dd, J1=8.0 Hz, J2=2.0 Hz, 1H, aromatic), 7.44-7.35 (m, 3H, aromatic), 7.34 (dd, J1=8.4 Hz, J2=0.8 Hz, 1H, aromatic), 7.13 (d, J=2.4 Hz, 1H, aromatic), 7.12 (d, J=8.4 Hz, 1H, aromatic), 7.04 (app. t, J1 7.2 Hz, 1H, aromatic), 6.91 (app. t, J=7.2 Hz, 1H, aromatic), 4.054 (s, 2H, CH₂Ar), 4.048 (s, 3H, OCH₃), 2.66 (s, 3H, ArCH₃); 13C NMR (100 MHz, (CD₃)₂CO) δ 162.4, 156.1, 137.7, 137.5, 137.0, 135.1, 134.8, 133.6, 132.3, 131.2, 131.1, 127.2, 126.0, 122.9, 121.3, 119.2, 118.6, 118.5, 114.2, 112.2, 111.3, 56.1, 30.0, 19.3; m/z calcd for C₂₄H₂₂N₂O₄S 434.1; found 435.1 [M+H]⁺. Purity of the compound was further confirmed by RP-HPLC by using method A: Rt=20.50 min (98%).

Synthesis of Compound 22a.

A mixture of compound 19 (30 mg, 0.10 mmol), benzenesulfonamide (19 mg, 0.12 mmol), EDC.HCl (31 mg, 0.16 mmol), and DMAP (22 mg, 0.18 mmol) in anhydrous CH₂Cl₂ (5 mL) was stirred at room temperature overnight. Upon

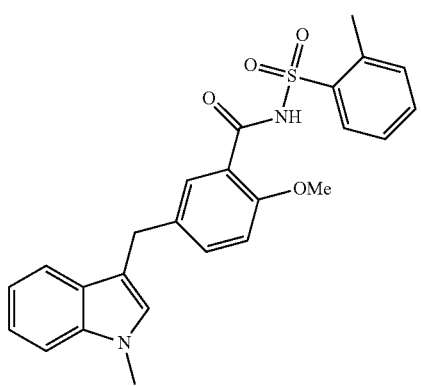 [SMILES: COc1ccc(Cc2cn(C)c3ccccc23)cc1C(=O)NS(=O)(=O)c1ccccc1C]

completion, the reaction mixture was diluted with H₂O and extracted with CH₂Cl₂ (3×). The combined organic layers were washed with brine, dried over MgSO₄, filtered, and concentrated. The crude product obtained was purified by column chromatography (SiO₂ gel, pure Hexanes to Hexanes:EtOAc/1:1, Rf 0.47 in Hexanes:EtOAc/1:1) to afford compound 22a (41 mg, 93%) as an off-white solid: ¹H NMR (400 MHz, CDCl₃) δ 10.42 (s, 1H, NH), 8.15 (m, 2H, aromatic), 8.01 (d, J=2.0 Hz, 1H, aromatic), 7.60 (tt, J1=7.6 Hz, J2=1.2 Hz, 1H, aromatic), 7.54-7.50 (m, 2H, aromatic), 7.40-7.37 (m, 2H, aromatic), 7.25 (d, J=8.4 Hz, 1H, aromatic), 7.17 (td, J1=8.4 Hz, J2=1.2 Hz, 1H, aromatic), 7.01 (td, J1=8.4 Hz, J2=1.2 Hz, 1H, aromatic), 6.87 (d, J=8.8 Hz, 1H, aromatic), 6.73 (s, 1H, aromatic), 4.00 (s, 2H, CH₂Ar), 3.98 (s, 3H, ArOCH₃), 3.69 (s, 3H, NCH₃); ¹³C NMR (100 MHz, CDCl₃) δ 162.4, 156.1, 139.0, 137.2, 135.3, 135.2, 133.7, 132.5, 128.8 (2 carbons), 128.6 (2 carbons), 127.5, 127.1, 121.6, 118.9, 118.8, 118.3, 113.4, 111.8, 109.2, 56.5, 32.6, 30.4; m/z calcd for C₂₄H₂₂N₂O₄S 434.1; found 435.1 [M+H]⁺. Purity of the compound was further confirmed by RP-HPLC by using method B: Rt=25.26 min (96%).

Synthesis of Compound 22b.

A mixture of compound 19 (30 mg, 0.10 mmol), o-toluenesulfonamide (21 mg, 0.12 mmol), EDC.HCl (31 mg, 0.16 mmol), and DMAP (22 mg,

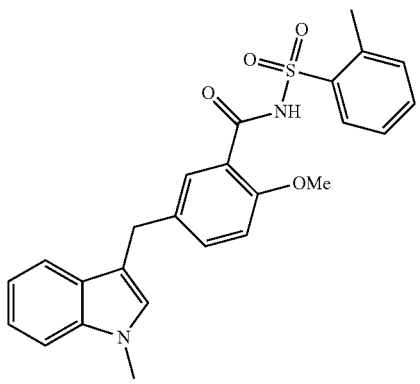 [SMILES: COc1ccc(Cc2cn(C)c3ccccc23)cc1C(=O)NS(=O)(=O)c1ccccc1C]

0.18 mmol) in anhydrous CH₂Cl₂ (5 mL) was stirred at room temperature overnight. Upon completion, the reaction mixture was diluted with H₂O and extracted with CH₂Cl₂ (3×). The combined organic layers were washed with brine, dried over MgSO₄, filtered, and concentrated. The crude product obtained was purified by column chromatography (SiO₂ gel, pure Hexanes to Hexanes:EtOAc/1:1, Rf 0.47 in Hexanes:EtOAc/1:1) to afford compound 22b (41 mg, 89%) as an off-white solid: ¹H NMR (400 MHz, CDCl₃) δ 10.42 (s, 1H, NH), 8.24 (dd, J1=8.0 Hz, J2=2.4 Hz, 1H, aromatic), 7.95 (d, J=2.4 Hz, 1H, aromatic), 7.46 (td, J1=7.2 Hz, J2=1.2 Hz, 1H, aromatic), 7.40 (d, J=2.8 Hz, 1H, aromatic), 7.38-7.35 (m, 2H, aromatic), 7.26-7.22 (m, 2H, aromatic), 7.16 (td, J1=7.2 Hz, J2=1.2 Hz, 1H, aromatic), 6.99 (td, J1=8.0 Hz, J2=1.2 Hz, 1H, aromatic), 6.88 (d, J=8.8 Hz, 1H, aromatic), 6.72 (s, 1H, aromatic), 4.00 (s, 3H, ArOCH₃), 3.98 (s, 2H, CH₂Ar), 3.68 (s, 3H, NCH3), 2.66 (s, 3H, ArCH₃); ¹³C NMR (100 MHz, CDCl₃) δ 162.4, 156.1, 137.4, 137.2, 137.0, 135.3, 135.2, 133.7, 132.5, 132.7, 132.5, 132.4, 132.3, 131.4, 128.1, 127.4, 127.1, 126.3, 126.2, 121.6, 118.9, 118.8, 118.4, 113.4, 111.8, 109.2, 56.5, 32.6, 30.4, 20.2; m/z calcd for C₂₅H₂₄N₂O₄S 448.2; found 449.1 [M+H]⁺. Purity of the compound was further confirmed by RP-HPLC by using method B: Rt=25.71 min (95%).

Synthesis of Compound 23a.

A mixture of compound 20 (25 mg, 0.073 mmol),

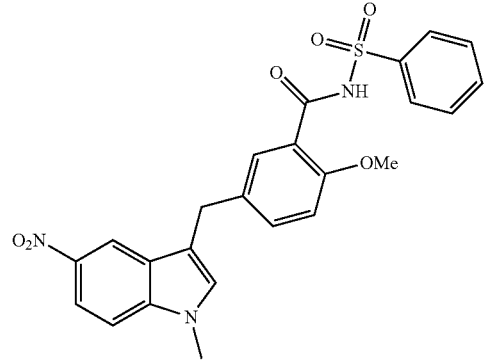 [SMILES: COc1ccc(Cc2cn(C)c3ccc([N+](=O)[O-])cc23)cc1C(=O)NS(=O)(=O)c1ccccc1]

benzenesulfonamide (14 mg, 0.088 mmol), EDC.HCl (22 mg, 0.11 mmol), and DMAP (16 mg, 0.13 mmol) in N anhydrous CH₂Cl₂ (5 mL) was stirred at room temperature OMe overnight. Upon completion, the reaction mixture was diluted with H₂O and extracted with CH₂Cl₂ (3×). The combined organic layers were washed with brine, dried over MgSO₄, filtered, and concentrated. The crude product obtained was purified by column chromatography (SiO₂ gel, CH₂Cl₂:MeOH/49:1, Rf 0.64 in CH₂C2:MeOH/19:1) to afford compound 23a (24 mg, 69%) as a yellow solid: ¹H NMR (400 MHz, CDCl₃) δ 10.38 (s, 1H, NH), 8.32 (d, J=2.4

Hz, 1H, aromatic), 8.13-8.10 (m, 2H, aromatic), 8.07 (dd, J1=8.8 Hz, J2=2.4 Hz, 1H, aromatic), 7.91 (d, J=2.4 Hz, 1H, aromatic), 7.59 (tt, J1=7.6 Hz, J2=2.0 Hz, 1H, aromatic), 7.53-7.48 (m, 2H, aromatic), 7.43 (dd, J1=8.8 Hz, J2=2.4 Hz, 1H, aromatic), 7.25 (d, J=9.6 Hz, 1H, aromatic), 6.93 (d, J=8.8 Hz, 1H, aromatic), 6.86 (s, 1H, aromatic), 4.01 (s, 5H, ArOCH$_3$, CH$_2$Ar), 3.75 (s, 3H, NCH$_3$); $^{13}$C NMR (100 MHz, CDCl$_3$) δ 162.3, 156.4, 141.2, 139.9, 138.9, 135.1, 133.9, 133.7, 132.5, 130.2, 128.8 (2 carbons), 128.5 (2 carbons), 126.7, 118.7, 117.5, 116.5, 116.3, 111.9, 109.2, 56.6, 33.1, 30.0; m/z calcd for C$_{24}$H$_{21}$N$_3$O$_6$S 479.1; found 480.1 [M+H]$^+$. Purity of the compound was further confirmed by RP-HPLC by using method B: Rt=24.48 min (97%).

Synthesis of Compound 23b.

A mixture of compound 20 (25 mg, 0.073 mmol), o-toluenesulfonamide (15 mg, 0.088 mmol), EDC.HCl (22 mg, 0.11 mmol), and DMAP (16 mg, 0.13 mmol) in anhydrous CH$_2$Cl$_2$ (5 mL) was stirred at room temperature overnight. Upon completion, the reaction mixture was diluted with H$_2$O and extracted with CH$_2$Cl$_2$ (3×). The

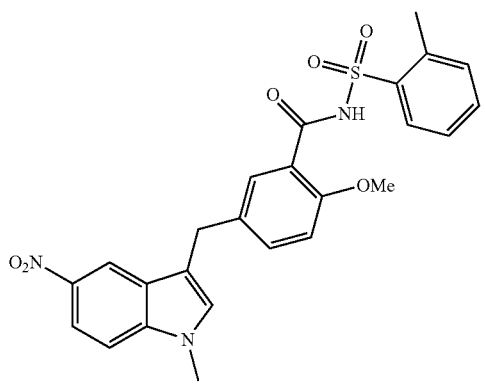 [SMILES: COc1ccc(Cc2cn(C)c3ccc([N+](=O)[O-])cc23)cc1C(=O)NS(=O)(=O)c1ccccc1C]

combined organic layers were washed with brine, dried over MgSO$_4$, filtered, and concentrated. The crude product obtained was purified by column chromatography (SiO2 gel, CH$_2$C2:MeOH/49:1, Rf 0.66 in CH$_2$Cl$_2$:MeOH/19:1) to afford compound 23b (26 mg, 72%) as a yellow solid: $^1$H NMR (400 MHz, CDCl$_3$) δ 10.39 (s, 1H, NH), 8.30 (d, J=2.4 Hz, 1H, aromatic), 8.21 (dd, J1=8.0 Hz, J2=1.2 Hz, 1H, aromatic), 8.06 (dd, J1=8.8 Hz, J2=2.4 Hz, 1H, aromatic), 7.86 (d, J=2.4 Hz, 1H, aromatic), 7.47-7.41 (m, 2H, aromatic), 7.35 (t, J=7.2 Hz, 1H, aromatic), 7.24 (d, J=8.8 Hz, 2H, aromatic), 6.95 (d, J=8.4 Hz, 1H, aromatic), 6.85 (s, 1H, aromatic), 4.03 (s, 3H, ArOCH$_3$), 4.00 (s, 2H, CH$_2$Ar), 3.74 (s, 3H, NCH$_3$), 2.65 (s, 3H, ArCH$_3$); $^{13}$C NMR (100 MHz, CDCl$_3$) δ 162.2, 156.3, 141.1, 139.9, 137.4, 137.0, 135.1, 134.0, 133.8, 132.4, 132.3, 131.4, 130.3, 126.7, 126.3, 118.7, 117.4, 116.4, 116.3, 112.0, 109.2, 56.6, 33.1, 30.0, 20.1; m/z calcd for C$_{25}$H$_{23}$N$_3$O$_6$S 493.1; found 494.0 [M+H]$^+$. Purity of the compound was further confirmed by RP-HPLC by using method B: Rt=25.04 min (98%).

Design and Synthesis of Novel Zafirlukast Derivatives

Several synthetic methods were reported for either linear or convergent synthesis of zafirlukast.[29, 30, 33-39] Here, the concise and linear synthesis of zafirlukast derivatives involved a C—C bond formation between various substituted indoles and benzoyl analogues followed by a subsequent sulfamidation step. The initial synthesis centered on creating zafirlukast derivatives 4a and 4b with variations on the arylsulfonamide domain as well as the elimination of the cyclopentyl carbamate of the indole of the parent molecule (Scheme 1). The alkylation of 1-methylindole in presence of silver oxide followed by ester hydrolysis resulted in compound 3 in 29% yield. The coupling of the acid 3 with both benzenesulfonamide and o-toluenesulfonamide generated target compounds 4a and 4b in 84 and 59% yields, respectively. The derivatives devoid of a methoxy group substituent on the benzoyl ring were synthesized according to Scheme 2. The condensation reaction between 4-formylbenzoate with both indole and 1-methylindole resulted in compounds 7 and 8 in 23% and 56% yields, respectively. The hydrolysis of these compounds followed by their coupling with both benzenesulfonamide and o-toluenesulfonamide generated derivatives 11a, 11b, and 12a in 58-100% yields. The synthesis of the final set of derivatives with modifications on the indole, benzoyl, and arylsulfonamide regions is depicted in Scheme 3. The condensation reaction between indole, 1-methylindole, and 1-methyl-5-nitroindole with compound 14, a commercially available molecule, generated compounds 15, 16, and 17 in 43-89% yields. Finally, hydrolysis and sulfamidation yielded derivatives 21a, 21b, 22a, 22b, 23a, and 23b in 20-95% yields.

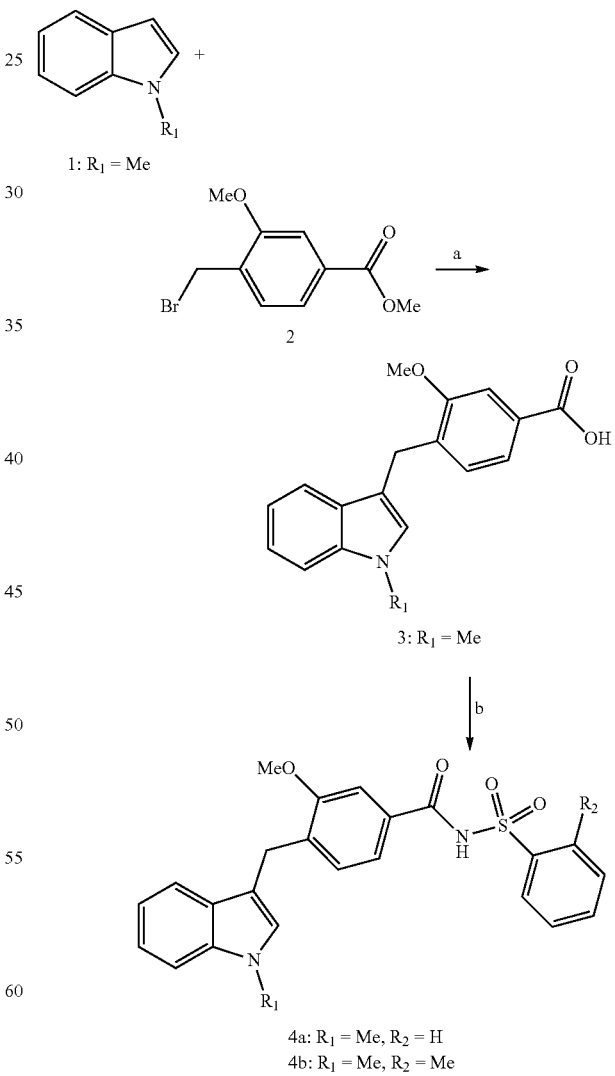

Scheme 1. The synthesis of zafirlukast derivatives 4a and 4b.

4a: R$_1$ = Me, R$_2$ = H
4b: R$_1$ = Me, R$_2$ = Me

Reaction conditions: (a) Ag$_2$O, dioxane, 60° C., then MeOH:THF:H$_2$O/ 5:1:1, KOH, room temperature, 29%; (b) arylsulfonamide, EDC•HCl, DMAP, CH$_2$Cl$_2$, room temperature, 59-84%.

Scheme 2. The synthesis of zafirlukast derivatives 11a, 11b, and 12a.
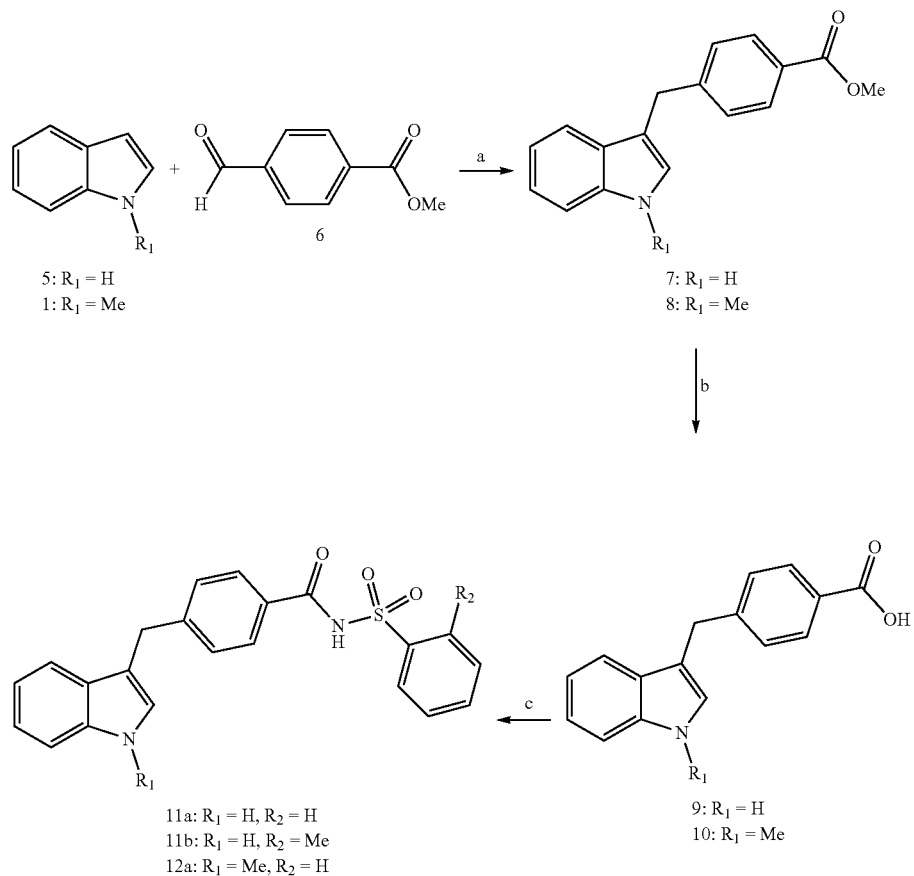
Reaction conditions: (a) formylbenzoate, Et₃SiH, TFA, CH₂Cl₂, 0° C. to room temperature, 23-56%; (b) MeOH:THF:H₂O/5:1:1, KOH, room temperature, 83-84%; (c) arylsulfonamide, EDC•HCl, DMAP, CH₂Cl₂, room temperature, 58%-quant.
Scheme 3. The synthesis of zafirlukast derivatives 21a, 21b, 22a, 22b, 23a, and 23b.
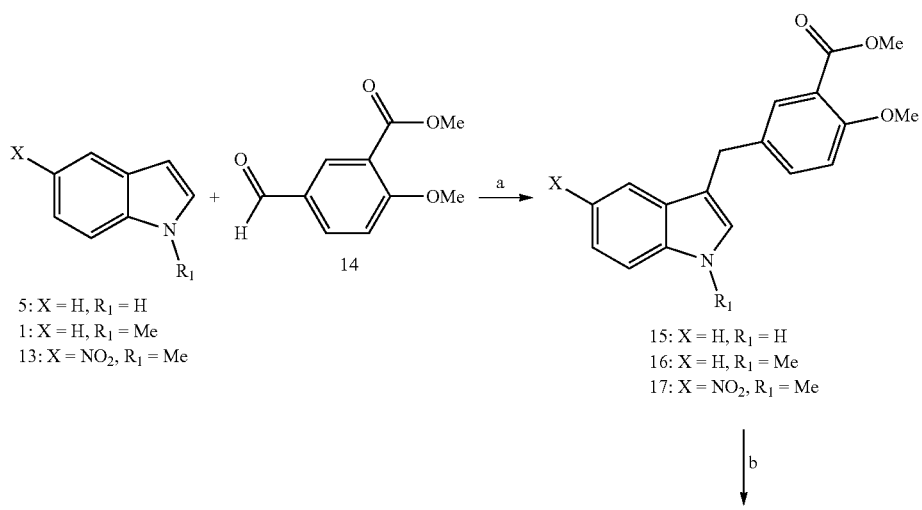

-continued

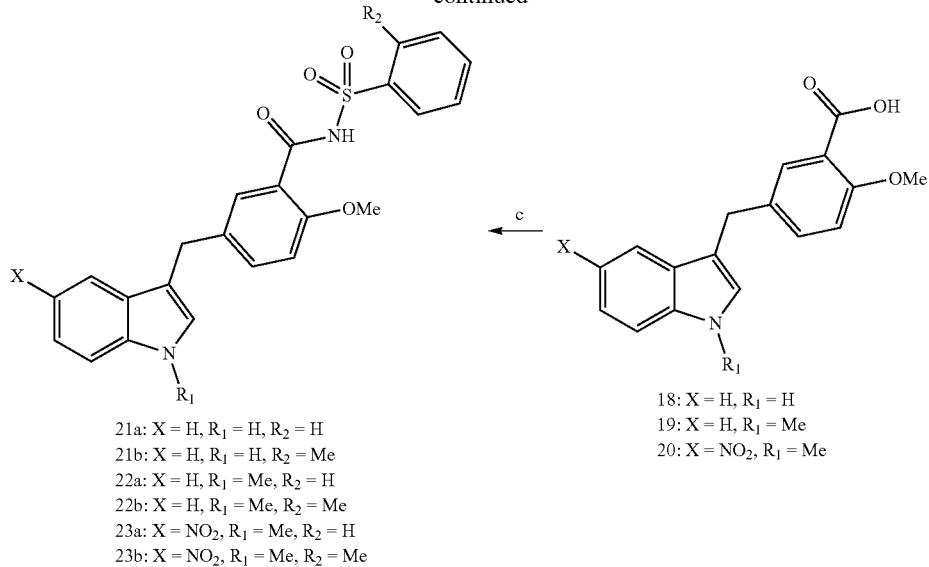

21a: X = H, R₁ = H, R₂ = H
21b: X = H, R₁ = H, R₂ = Me
22a: X = H, R₁ = Me, R₂ = H
22b: X = H, R₁ = Me, R₂ = Me
23a: X = NO₂, R₁ = Me, R₂ = H
23b: X = NO₂, R₁ = Me, R₂ = Me

18: X = H, R₁ = H
19: X = H, R₁ = Me
20: X = NO₂, R₁ = Me

Reaction conditions: (a) methyl 5-formyl-2-methoxybenzoate, Et₃SiH, TFA, CH₂Cl₂, 0° C. to room temperature, 43-89%; (b) MeOH:THF:H₂O/5:1:1, KOH, 65° C., 87-93%; (c) arylsulfonamide, EDC•HCl, DMAP, CH₂Cl₂, room temperature, 20-95%.

Bacterial Strains and Growth Conditions.

The following bacterial strains were used in these studies: *Porphyromonas gingivalis* 381, *Actinomyces naeslundii* ATCC 49340, *Streptococcus sanguinis* ATCC 10556, *Veillonella parvula* ATCC 10790, *Aggregatibacter actinomycetemcomitans* JP2, and *Fusobacterium nucleatum* ATCC 25586. All bacterial strains were initially grown on blood agar plates (BBL, Becton Dickinson, Sparks, Md., USA) from a frozen stock and incubated in appropriate aerobic (for *S. sanguinis*) or anaerobic (for *P. gingivalis, A. naeslundii, V. parvula, A. actinomycetemcomitans*, and *F. nucleatum*) conditions at 37° C. for 24 h or 3 days, respectively. Then, a liquid culture was started for each strain in 3 mL of Brain Hearth infusion (BHI) broth alone or supplemented with 5 µg/mL of hemin and 1 µg/mL of menadione in the case of *P. gingivalis*. Overnight cultures were inoculated in fresh broth and allowed to reach logarithmic growth for 3-4 h, time at which antimicrobial activity of different treatments was evaluated.

Biological Assays

Effect of Zafirlukast Derivatives on Bacterial Viability.

Initial screening for testing the antimicrobial effect of zafirlukast derivatives (4a, 4b, 11a, 11b, 12a, 21a, 21b, 22a, 22b, 23a, and 23b) was performed using the colorimetric water-soluble tetrazolium-1 (WST-1) assay, which serves as a surrogate marker for cell proliferation and viability. Bacterial strains ($10^6$/well) grown logarithmically in broth (90 µL) using 96-wells plates, were exposed to different treatments for 2 h and then 15 µL of WST-1 reagent (Roche, Manheim, Germany) were added to each well. Plates were incubated for 2 h under appropriate culture conditions and then absorbance was measured at 450 nm, with a reference wavelength of 600 nm, using SpectraMax M2 plate reader (Molecular Devices, Sunnyvale, Calif., USA). The percentage of inhibitory effect (i.e., % growth inhibition) was calculated using the optical densities (ODs) of bacterial metabolic activity, under different experimental conditions according to the following formula: 100×[OD (control)−OD (experimental)/OD (control)]. For *P. gingivalis*, control cultures were treated only with medium and experimental cultures treated with DMSO (vehicle for zafirlukast and its derivatives) and 1 µg/mL of the antibiotic tetracycline. These data are presented in FIG. 2. When tested against *A. naeslundii, A. actinomycetemcomitans, S. sanguinis, V. parvula*, and *F. nucleatum* control cultures were treated only with medium and experimental cultures were treated with DMSO (vehicle for zafirlukast and its derivatives), antibiotic penicillin/streptomycin −1× (100 U/mL of penicillin and 100 µg/mL of streptomycin) for Gram-positives and 1 µg/mL of tetracycline for Gram-negative anaerobic bacteria. These data are presented in FIG. 3.

Bactericidal Effect of Zafirlukast Derivatives on *P. gingivalis*.

Figure 4:
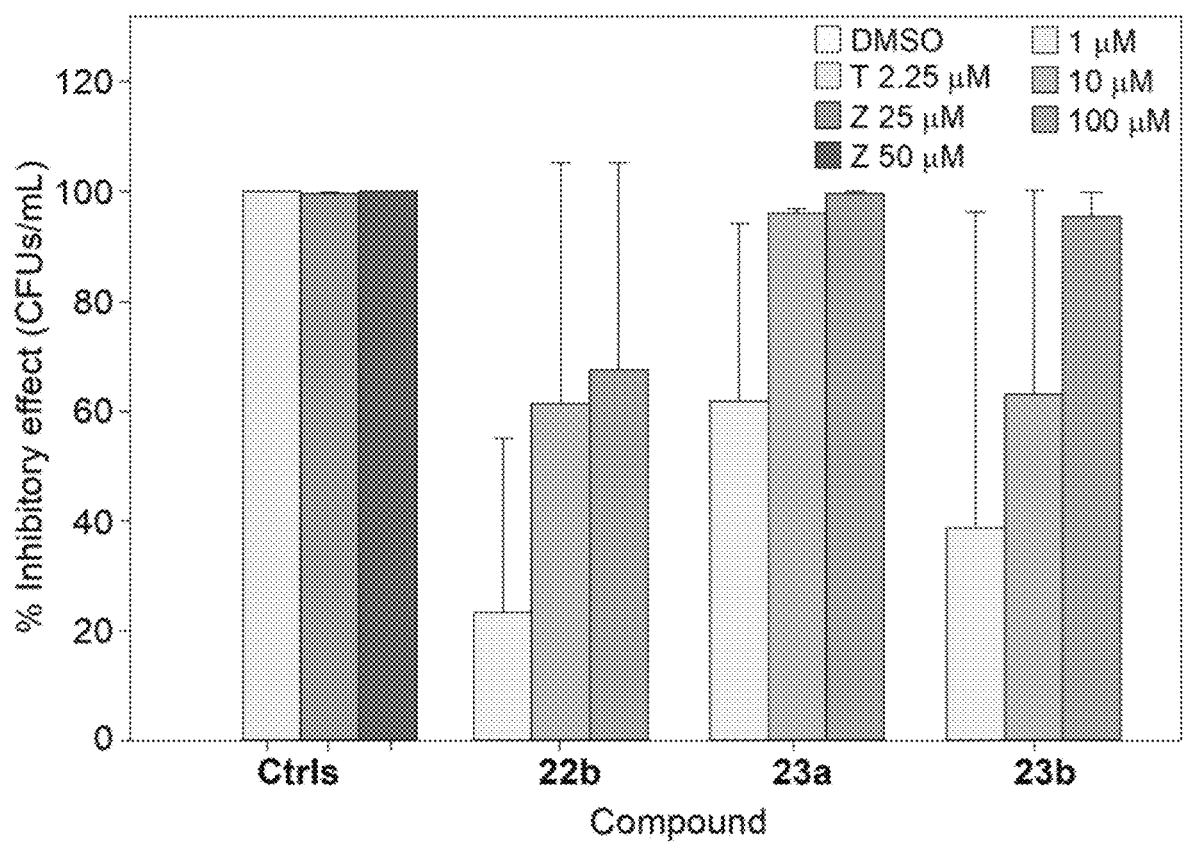
FIG. 4. Bactericidal effect of zafirlukast derivatives against *P. gingivalis*. *P. gingivalis* ($10^6$ cells) exponentially growing in appropriate medium and anaerobic conditions was exposed to zafirlukast (Z) derivatives 22b, 23a, and 23b (1, 10, and 100 µM) for 24 h. Diluted bacteria [1:400] were seeded in blood agar plates, incubated for 7 days and colony-forming units (CFUs) were counted. Percentage of inhibitory effect calculated comparing treatment groups versus bacteria only in growth medium. Bacteria incubated with antibiotic tetracycline (T, 2.25 µM) and zafirlukast (Z, 25 and 50 µM) were used as positive controls. Bacteria incubated with DMSO were used as a negative control. Data represents the mean of 5-6 replicates per condition.

The bactericidal effect of zafirlukast derivatives 22b, 23a, and 23b (which exhibited the best antimicrobial potential at lower concentrations determined by WST-1) was evaluated by determination of colony forming units per milliliter (CFUs/mL) after different treatments. *P. gingivalis* ($10^6$/well) grown in appropriate medium and anaerobic conditions was exposed to zafirlukast derivatives dissolved in DMSO for 24 h and further 50 µL of bacterial culture dilutions (1:400) were spread onto blood agar plates. Numbers of CFUs were obtained after 7 days of incubation in appropriate anaerobic conditions. Bacteria exposed to only medium or DMSO were used as a negative controls and bacteria exposed to 2.25 µM of tetracycline (equivalent to 1 µg/mL, a standard concentration usually used for this control) and zafirlukast at 25 and 50 µM diluted in DMSO (concentrations that previously showed antimicrobial effect against *P. gingivalis*) were also used as positive controls.[2] These data are presented in FIG. 4.

Cytotoxic effect of zafirlukast derivatives in oral epithelial cells. The immortalized oral keratinocyte cell line OKF6/hTERT (OKF6) was used for viability assays in response to zafirlukast derivatives 22b, 23a, and 23b as previously reported.[3,4] Cells were cultured in keratinocyte-serum free medium (SFM) supplemented with bovine pituitary extract (25 µg/mL) and recombinant epidermal growth factor (0.2 ng/mL) (Ker-SFM). Cells were maintained at 37° C. in a humidified incubator with 5% CO2.

For viability assays, cells ($10^5$ cells/well) were seeded in 96-wells plates overnight in Ker-SFM and further exposed to zafirlukast at 25 µM or its derivatives at 1 and 10 µM dissolved in DMSO for 24 h. Cells were then harvested by trypsinization, washed with DMEM medium supplemented with 5% fetal bovine serum at 1100 rpm and resuspended in fresh Ker-SFM. Equal volumes of cell suspension and trypan blue were mixed and 10 µL evaluated in the automated cell counter (Countess II FL) (Life Technologies, Singapure) to determine percentage of alive and death cells. These experiments were performed in two independent experiments by duplicate. These data are presented in FIG. 5 and Table 1. To further determine the IC50 values for zafirlukast derivatives 22b, 23a, and 23b, the same assay was performed in triplicate using the following concentrations of compounds: 0, 1, 2.5, 5, 10, 15, 20, 25, 50, and 100 µM. These data are presented in FIG. 6 and Table 2. The IC50 values were calculated by using the Quest Graph™ $IC_{50}$ calculator (ATT Bioquest, Inc, https://www.aatbio.com/tools/ic50-calculator).

TABLE 1

Percentage of OKF6 oral epithelial cells alive and dead after 24 h of exposure to compounds 22b, 23a, and 23b.[a]

| Cpd and concentration used | Alive (%) | Dead (%) |
|---|---|---|
| Medium | 83.0 ± 2.6 | 17.0 ± 2.6 |
| DMSO | 85.3 ± 4.6 | 14.8 ± 4.6 |
| Zafirlukast 25 µM | 17.3 ± 5.2 | 82.8 ± 5.2 |
| 22b 1 µM | 91.5 ± 1.7 | 8.5 ± 1.7 |
| 22b 10 µM | 40.8 ± 16.6 | 59.3 ± 16.6 |
| 23a 1 µM | 79.5 ± 16.4 | 20.5 ± 16.4 |
| 23a 10 µM | 73.8 ± 4.1 | 26.3 ± 4.1 |
| 23b 1 µM | 82.8 ± 9.5 | 17.3 ± 9.5 |
| 23b 10 µM | 48.3 ± 17.5 | 51.8 ± 17.5 |

Figure 5:
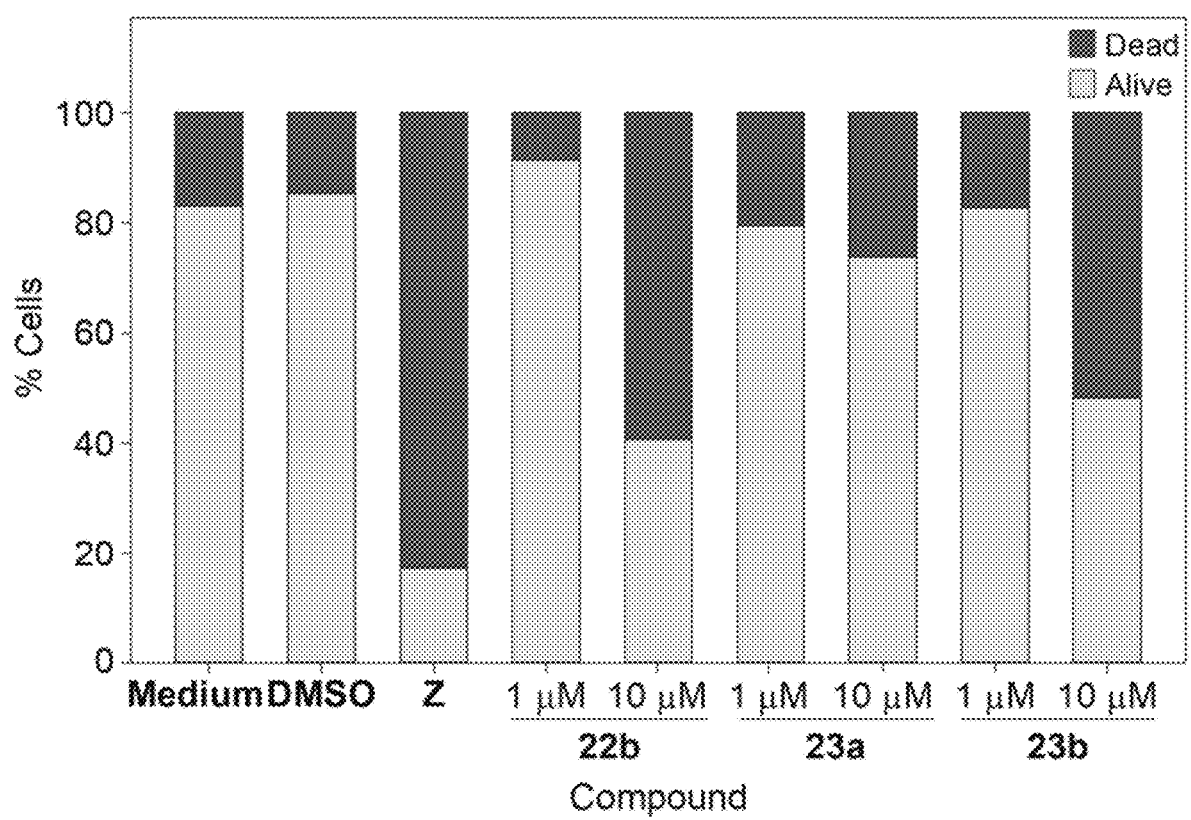
FIG. 5. Preliminary study of effect of zafirlukast derivatives on cell viability of oral epithelial cells. OKF6 cells were exposed to zafirlukast (Z, 25 µM) or its derivatives 22b, 23a, and 23b at 1 and 10 µM for 24 h and cell viability tested using Trypan blue with the automated cell counter (Countess II FL. Life Technology). Trypan blue data represents a mean from two independent experiments by duplicate.

[a]The values presented were used to generate FIG. 5.

TABLE 2

Percentage of OKF6 oral epithelial cells alive after 24 h of exposure to compounds 22b, 23a, and 23b.[a]

| Cpd and concentration used | 22b | 23a | 23b |
|---|---|---|---|
| Medium | 78.7 ± 4.0 | 86.0 ± 7.0 | 93.3 ± 1.2 |
| Zafirlukast 25 µM | 5.3 ± 3.1 | 11.7 ± 10.8 | 9.3 ± 1.5 |
| 0 µM | 77.7 ± 17.5 | 70.3 ± 12.5 | 89.3 ± 5.5 |
| 1 µM | 69.3 ± 9.6 | 68.0 ± 5.0 | 83.7 ± 9.1 |
| 2.5 µM | 41.0 ± 1.0 | 70.7 ± 10.3 | 87.7 ± 3.8 |
| 5 µM | 66.0 ± 5.6 | 55.3 ± 8.1 | 87.0 ± 2.6 |
| 10 µM | 38.3 ± 4.9 | 49.0 ± 16.1 | 83.0 ± 5.3 |
| 15 µM | 41.0 ± 17.3 | 50.3 ± 9.5 | 79.0 ± 5.3 |
| 20 µM | 22.7 ± 11.7 | 48.0 ± 6.1 | 75.3 ± 3.8 |
| 25 µM | 47.0 ± 20.0 | 54.0 ± 7.8 | 77.0 ± 2.6 |
| 50 µM | 33.0 ± 15.1 | 45.3 ± 13.1 | 69.0 ± 7.5 |
| 100 µM | 12.3 ± 11.0 | 15.7 ± 7.1 | 58.7 ± 4.2 |

Figure 6:
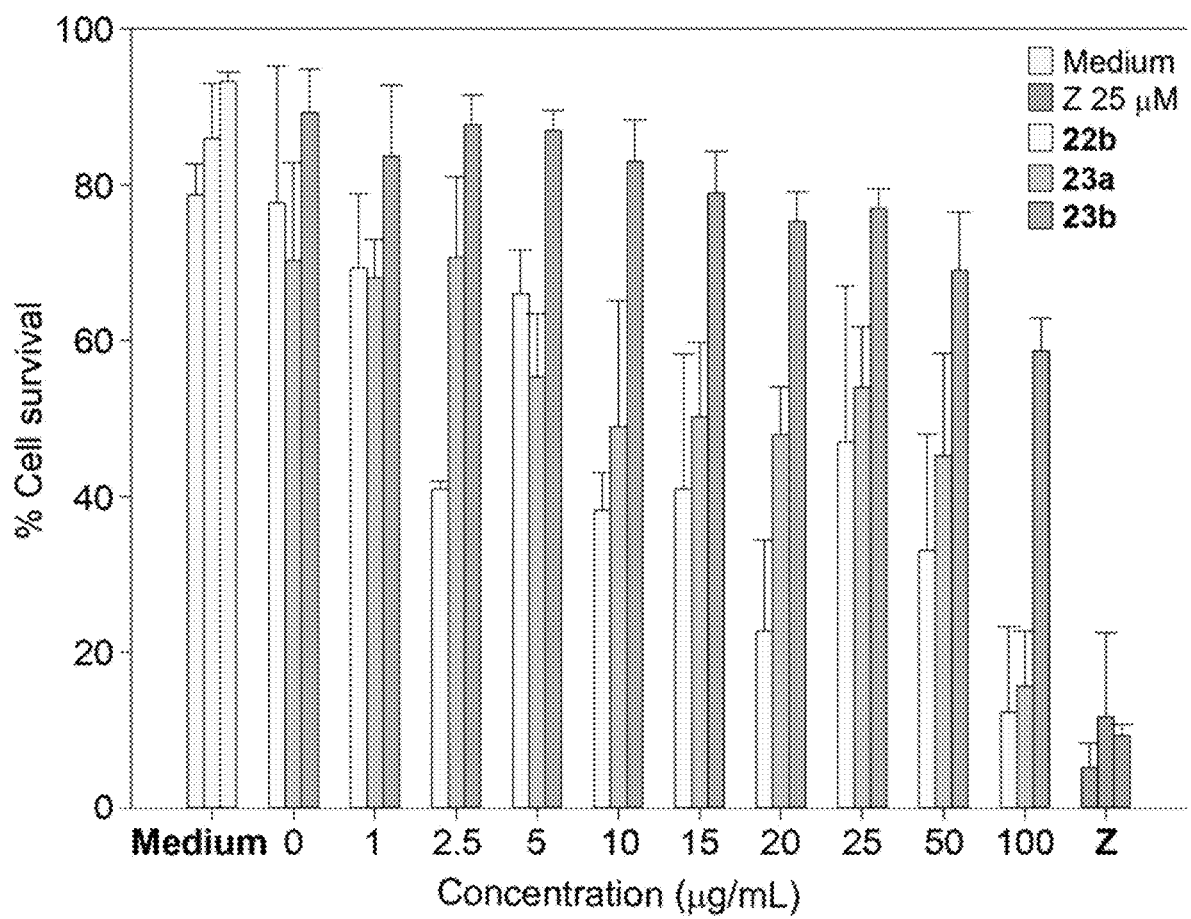
FIG. 6. Effect of zafirlukast derivatives on cell viability of oral epithelial cells. OKF6 cells were exposed to zafirlukast (Z, 25 μM) or its derivatives 22b, 23a, and 23b at different concentrations (0, 1, 2.5, 5, 10, 15, 20, 25, 50, and 100 μM) for 24 h and cell viability tested using Trypan blue with the automated cell counter (Countess II FL. Life Technology). Data represents a mean and SD from experiments performed in triplicate.

[a]The values presented were used to generate FIG. 6.

Cytotoxic effects of zafirlukast derivatives were confirmed by flow cytometry analysis (FACS). After different treatments, attached OKF6 cells were harvested by trypsinization and mixed with cells that were previously rescued from supernatants. Cells were washed with PBS at 1100 rpm for 5 min and further labeled with 5 µL of FITC-Annexin V and 5 µL of propidium iodide (BD Pharmingen, San Jose, Calif.) for 15 min at room temperature. Labeled cells were analyzed by FACS, with at least 10,000 events read at wavelengths averaging 488 nm for excitation and 530 nm for emission in a flow cytometer FACSCalibur (Becton Dickinson, San Jose, Calif.). These data are presented in FIG. 7 and Table 3.

TABLE 3

Percentage of OKF6 oral epithelial cells alive and dead (apoptosis and necrosis) after 24 h of exposure to compounds 22b, 23a, and 23b.[a]

| Cpd and concentration used | Viable | Apoptosis (%) | Necrosis (%) |
|---|---|---|---|
| DMSO | 85.9 ± 2.2 | 10.3 ± 6.9 | 3.73 ± 5.92 |
| Zafirlukast 25 µM | 8.53 ± 3.08 | 90.8 ± 2.5 | 0.65 ± 0.58 |
| 22b 1 µM | 74.1 ± 18.1 | 23.7 ± 16.6 | 2.16 ± 1.62 |
| 22b 10 µM | 69.1 ± 18.9 | 29.6 ± 19.1 | 1.37 ± 0.39 |
| 23a 1 µM | 60.9 ± 27.4 | 38.5 ± 27.5 | 0.69 ± 0.46 |
| 23a 10 µM | 53.2 ± 29.0 | 44.2 ± 26.9 | 2.81 ± 2.31 |
| 23b 1 µM | 74.4 ± 13.8 | 24.8 ± 13.9 | 1.08 ± 0.17 |
| 23b 10 µM | 61.7 ± 22.2 | 35.8 ± 21.3 | 2.23 ± 1.18 |

Figure 7:
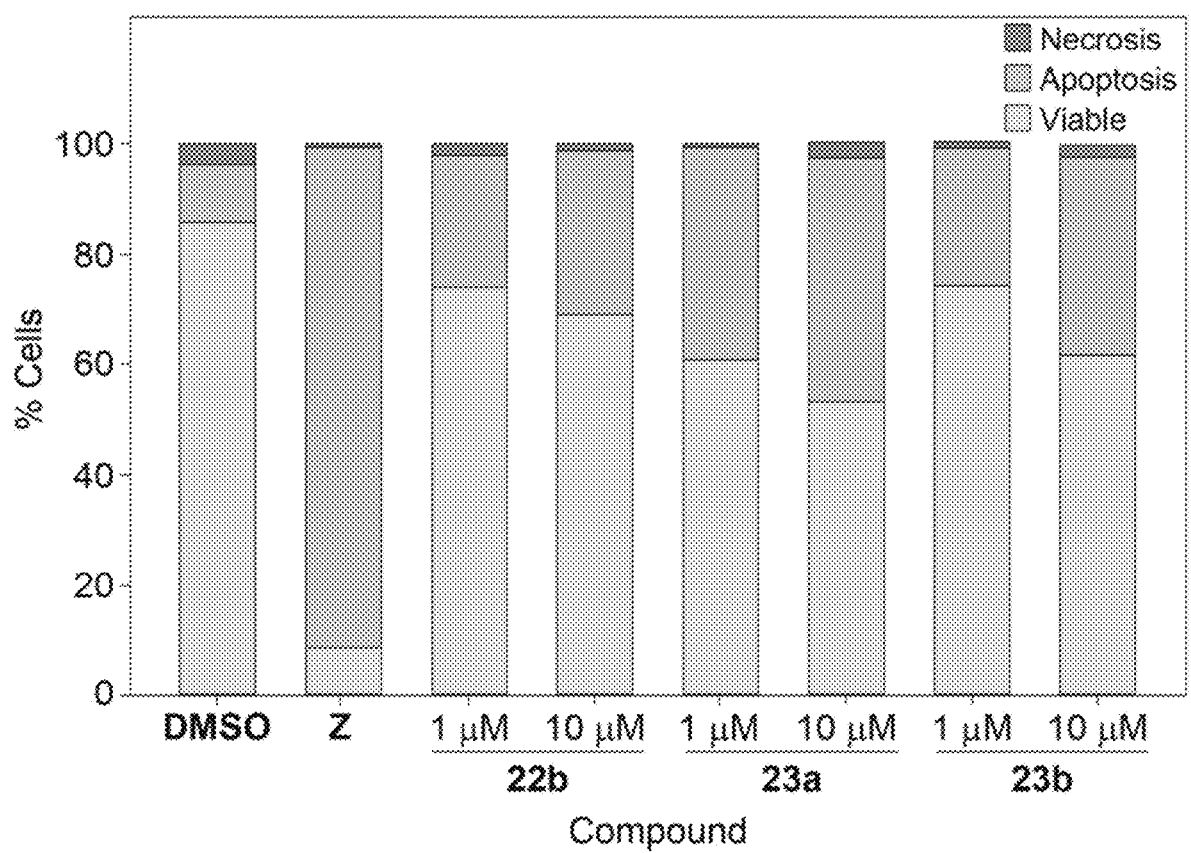
FIG. 7. Effect of zafirlukast derivatives on cell viability of oral epithelial cells (apoptosis and necrosis). OKF6 cells were exposed to zafirlukast (Z, 25 μM) and its derivatives 22b, 23a, and 23b at different concentrations for 24 h and cell viability tested by flow cytometry using FITC-Annexin V apoptosis detection kit (BD Pharmingen). The FACS data was generated by analyzing at least 10,000 events per condition in duplicates from two independent experiments.

[a]The values presented were used to generate FIG. 7.

In Vitro Antibacterial Testing.

Figure 2:
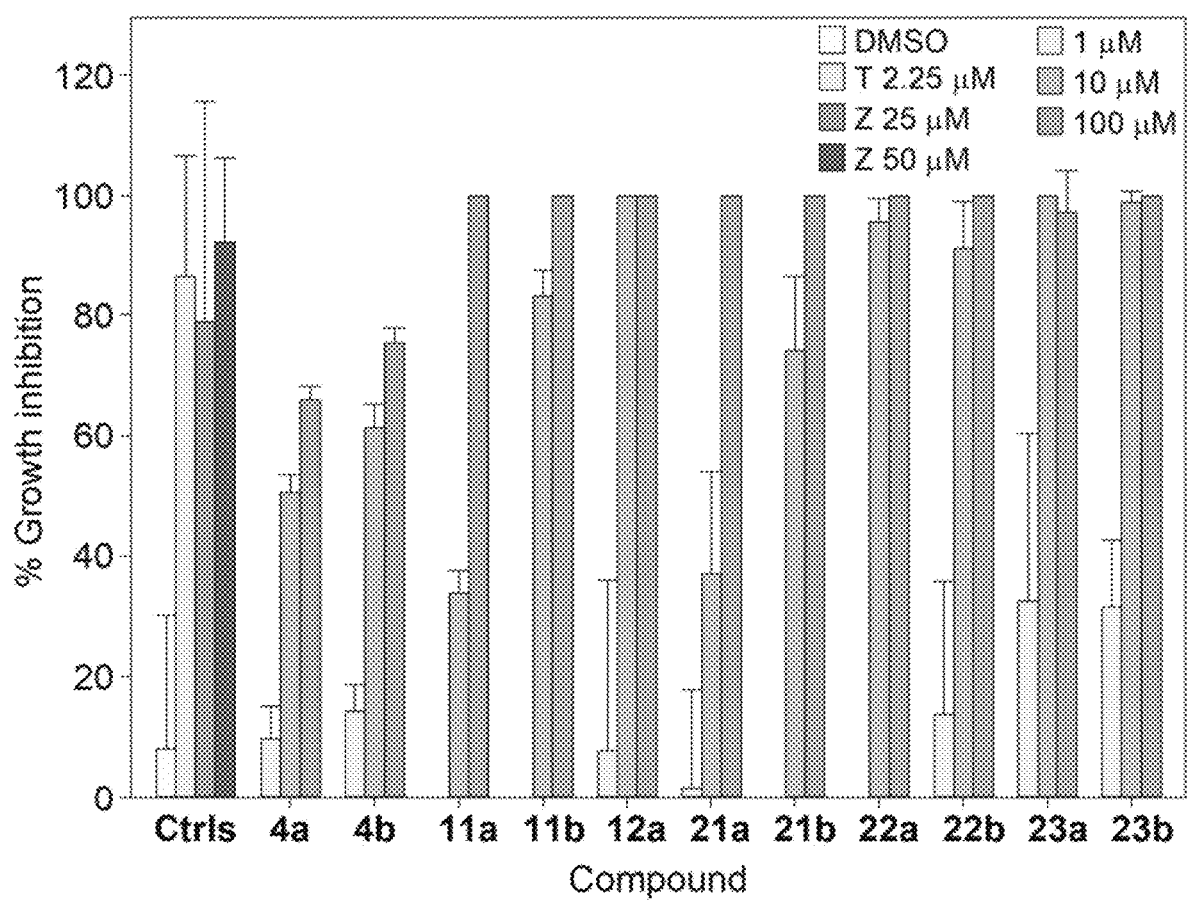
FIG. 2. Screening for antimicrobial effect of zafirlukast derivatives against *P. gingivalis*. *P. gingivalis* ($10^6$ cells) exponentially growing in appropriate medium and anaerobic conditions was exposed to zafirlukast (Z) derivatives 4a, 4b, 1a, 11b, 12a, 21a, 21b, 22a, 22b, 23a, and 23b (1, 10, and 100 µM) for 24 h. Bacteria incubated with tetracycline (T, 2.25 µM equivalent to 1 µg/mL) or zafirlukast (Z, 25 and 50 µM) were used as positive controls. Bacteria incubated with DMSO were used as a negative control. Data represents the mean inhibitory effect versus bacteria growing only in medium from 6 replicates per condition determined by a colorimetric WST-1 assay.

The antibacterial activity of the zafirlukast derivatives 4a, 4b, 11a, 11b, 12a, 21a, 21b, 22a, 22b, 23a, and 23b was first evaluated against *P. gingivalis* 381 at concentrations 1, 10, and 100 µM (FIG. 2). Commercially available drugs such as zafirlukast (at 25 and 50 µM) and tetracycline (at 2.25 µM) were used as positive controls for comparison. By a rapid survey of the data presented in FIG. 2, it could be conclude that all the zafirlukast derivatives exhibited 100% growth inhibition with the exception of compounds 4a and 4b at the highest concentrations tested. For compounds 4a and 4b slightly more than 60% growth inhibition at 100 µM as observed. At 10 µM, compounds 11a, 11b, 21a, and 21b displayed approximately 40%, 90%, 40%, and 80% growth inhibition, respectively. For the most active compounds 12a, 22a, 22b, 23a, and 23b 90-100% growth inhibition at 10 µM was observed. More importantly, the active compounds 12a, 22a, 22b, 23a, and 23b exhibited either comparable or, in most of the cases, enhanced antibacterial activity against *P. gingivalis* when compared to the control drugs zafirlukast and tetracycline. Compounds 22b, 23a, and 23b even displayed growth inhibition (15-40%) at 1 µM. These three compounds were therefore selected for further studies.

By a more in-depth analysis of the data presented in FIG. 2, important structural features required for zafirlukast derivatives' activity could be establish by SAR. The analysis was performed as follows. For each of the three series of derivatives (series 1: 4a-4b, series 2: 11a-12a, and series 3: 21a-23b, as presented in Schemes 1-3, respectively), each derivative was compared to the parent zafirlukast and then compared amongst themselves, the compounds within the series. For series 1, the removal of cyclopentyl carbamate group from the parent drug zafirlukast, as in compound 4b, resulted in reduced activity (i.e., reduced growth inhibition). The elimination of a methyl group from the arylsulfonamide scaffold of 4b (compound 4a) had no diminishing effect on the activity compared to 4b. In the case of series 2, the removal of the cyclopentyl carbamate group, methoxy group from benzoyl scaffold, as well as methyl group from the indole of zafirlukast resulted in a compound 11b with reduced activity. Exclusion of the methyl group from the arylsulfonamide of 11b (compound 11a) resulted in further loss of activity. Reinstating the methyl group of the indole of compound 11a yielded derivative 12a with substantially improved activity, which is comparable to zafirlukast and tetracycline. In the case of derivatives 21a, 21b, 22a, 22b, 23a, and 23b (series 3), permanent modifications were made in the substitution patterns of the benzoyl ring (position of methoxy and carboxylate group) of zafirlukast. The replacement of the cyclopentyl carbamate group with a nitro moiety (compound 23b) resulted in a compound with superior activity to zafirlukast. The removal of the methyl group from the arylsulfonamide of compound 23b (compound 23a) had no undesirable effect on the activity compared to compound 23b. Similarly, the elimination of the nitro group from compound 23b (compound 22b) was not detrimental to the activity of compound 22b. Further exclusion of the methyl group from the arylsulfonamide of derivative 22b (compound 22a) also had no negative effect on activity. Removal of the methyl group from the indole of compounds 22a and 22b resulted in derivatives 21a and 21b, respectively, with reduced activity in comparison.

Figure 3:
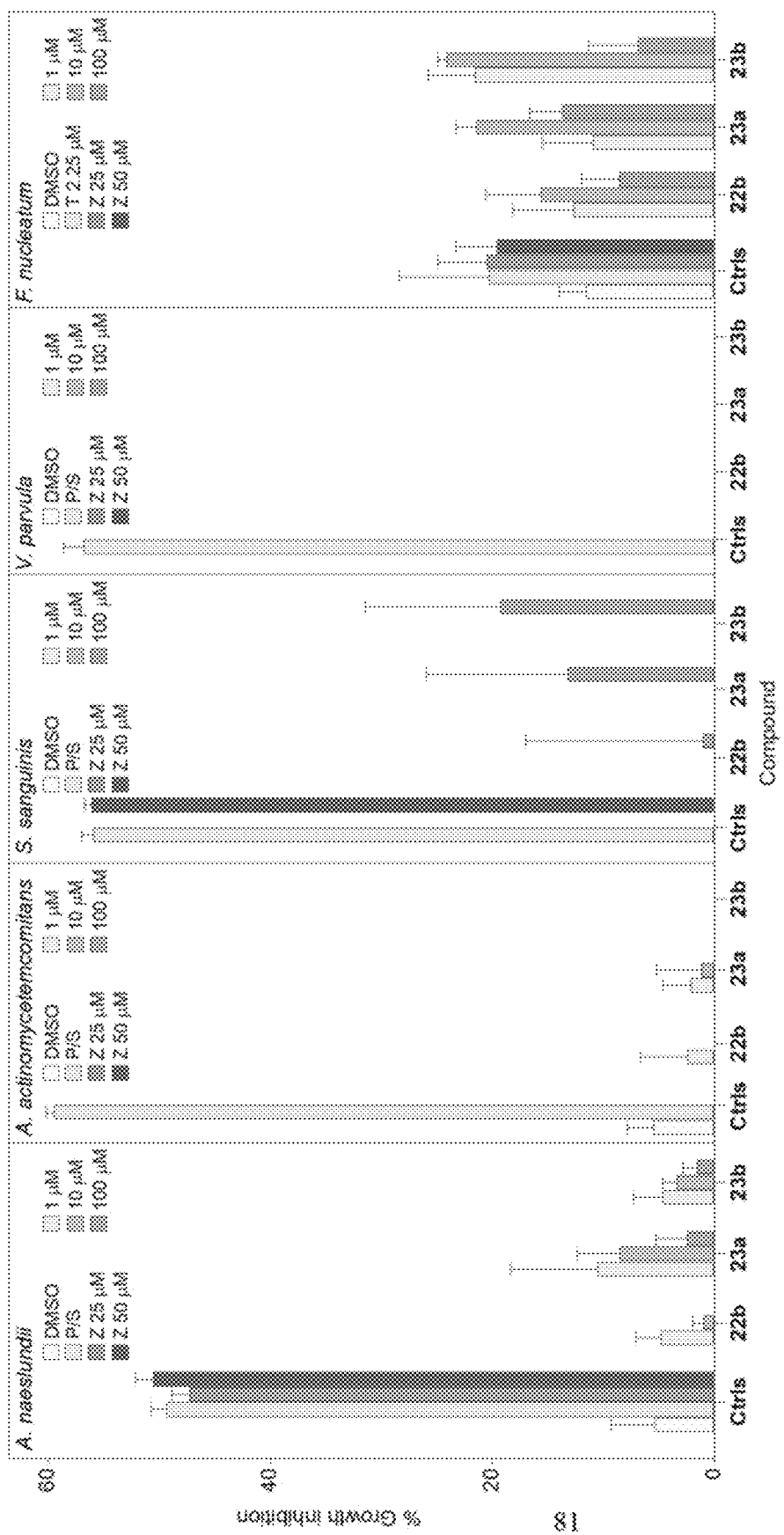
FIG. 3. Antimicrobial effect of zafirlukast derivatives against oral bacterial species. Oral bacterial species ($10^6$ cells) exponentially growing in appropriate medium and aerobic/anaerobic conditions were exposed to zafirlukast (Z) derivatives 22b, 23a, and 23b (1, 10, and 100 µM) for 24 h. Bacteria incubated with antibiotic (2.25 µM of tetracycline (T) equivalent to 1 µg/mL for *F. nucleatum* or 100 U/mL of penicillin+100 µg/mL of streptomycin (P/S) for all other bacteria) or zafirlukast (Z, 25 and 50 µM) were used as positive controls and bacteria incubated with DMSO were used as a negative control. Data represents the mean inhibitory effect versus bacteria growing only in medium from 6 replicates per condition determined by a colorimetric WST-1 assay.

In order to find whether zafirlukast derivatives were selective against *P. gingivalis*, the best compounds 22b, 23a, and 23b were then tested against other oral Gram-positive and Gram-negative bacteria, such as *Actinomyces naeslundii, Aggregatibacter actinomycetemcomitans, Streptococcus sanguinis, Veillonella parvula*, and *Fusobacterium nucleatum* (FIG. 3). Except for the minimal activity displayed against *S. sanguinis* and *F. nucleatum* (20%), none of the synthesized zafirlukast derivatives exhibited any activity, which suggests antibacterial selectivity for *P. gingivalis*.

To determine if the antibacterial activity of the zafirlukast derivatives was bacteriostatic or bactericidal, a colony forming units (CFUs) assay was performed by exposing compounds 22b, 23a, and 23b against *P. gingivalis* for a 24-h period followed by seven days of incubation (FIG. 4). *P. gingivalis* incubated with the antibiotics tetracycline (T, 2.25 µM) and zafirlukast (Z, 25 and 50 µM) were used as positive controls, whereas *P. gingivalis* incubated with DMSO was used as a negative control. Compounds 23a and 23b were found to be bactericidal at 100 µM against *P. gingivalis*. With its 100% growth inhibition at 10 µM, compound 23a displayed even superior activity than the control drug zafirlukast used at higher concentrations (25-50 µM). Compound 23a was found to be extremely potent as it exhibited close to 60% growth inhibition even at 1 µM.

Effect of Zafirlukast Derivatives on Cell Viability of Oral Epithelial Cells.

The oral epithelial cells provide a number of important functions such as protection against microorganisms, external aggressions, toxic materials, and prevention against mechanical damages. The drugs designed to target bacterial cells may cause unwanted toxicity to mammalian cells. Therefore, it is a crucial to consider selectivity as a parameter while developing antibacterial agents. For determining the selectivity of the zafirlukast derivatives synthesized, the most active compounds 22b, 23a, and 23b were tested against immortalized oral keratinocyte cell line OKF6, along with zafirlukast as a control.[40-43] A preliminary LIVE/DEAD assay was performed after incubating the cells with compounds 22b, 23a, and 23b for 24 h (FIG. 5). For compounds 22b, 23a, and 23b, 70-90% cell viability at 1 µM was observed. An increase in concentration from 1 µM to 10 µM resulted in more cell death with the exception of treatment with compound 23a. The IC$_{50}$ values for compounds 22b, 23a, and 23b were also determined in a similar assay performed in triplicate using 0, 1, 2.5, 5, 10, 15, 20, 25, 50, and 100 µM of the molecules, and were found to be 16 µM, 54 µM, and >100 µM (estimated at ~230 µM), respectively (FIG. 6 and Table 2). The effect of zafirlukast derivatives on cell viability of oral epithelial cells was further confirmed by flow cytometry analysis (FIG. 7). Fifty (50)-70% cell viability was observed in the case of compounds 22b, 23a, and 23b at the concentration range that exhibited antimicrobial activity (1-10 µM). Based on these assays it can be concluded that the synthetic derivatives 22b, 23a, and 23b displayed less cytotoxicity when compared to parent drug zafirlukast.

In summary, a linear synthesis of novel zafirlukast derivatives with modifications on the indole, arylsulfonamide, and benzoyl scaffolds was carried out. In addition, a detailed study of the antibacterial activity of zafirlukast derivatives 4a, 4b, 11a, 11b, 12a, 21a, 21b, 22a, 22b, 23a, and 23b against *P. gingivalis* was performed. Commercially available drugs, zafirlukast (Z) and tetracycline (T) were used as positive controls. From the SAR studies, three leading candidates 22b, 23a, and 23b were identified, which displayed excellent activity against *P. gingivalis* with 90-100% growth inhibition at a lower concentration of 10 µM. In most cases, these derivatives exhibited either comparable or enhanced antibacterial activity against *P. gingivalis* when compared to the control drugs zafirlukast and tetracycline. The structural modifications made on compounds 22b, 23a, and 23b yielded superior activity compared to zafirlukast. From the SAR study, it was concluded that the N-methylindole, benzoyl ring, and arylsulfonamide scaffolds of zafirlukast were flexible to changes in their substituents and substitution patterns.

The complete removal or the substitution of the cyclopentyl carbamate group as well as the elimination of the methyl group of the arylsulfonamide moiety had positive impact on their activity. Whereas in the case of benzoyl ring, changes in substitution pattern resulted in derivatives with better activity. The best compounds were found to be selective for *P. gingivalis* as they exhibited minimal activity against other oral bacterial species.

The bactericidal activity of the compounds 23a and 23b was confirmed by exposing them to *P. gingivalis* for 24 h. In addition, these compounds also exerted minimal toxicity against oral epithelial cells. There are still some interesting SAR to be done in order to optimize the lead compounds reported in this study. The methyl group on the indole ring of the active compounds could be replaced by other alkyl chains as well as aromatic ring systems. The arylsulfonamide moiety offers opportunity to explore various ortho-, meta-, and para-substitution patterns with methyl group and halogens.

The nitro group on the active compounds 23a and 23b provides a handle for further structural modifications, as it can be reduced and tagged with a fluorescent moiety in order to investigate the mechanism of action of these molecules. Overall, the novel zafirlukast derivatives according to the presently-disclosed subject matter provide unique and specific antibacterial agent against *P. gingivalis* and periodontal disease.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Each of the following references is herein incorporated by reference in its entirety.

1. Eke, P. I.; Dye, B. A.; Wei, L.; Slade, G. D.; Thornton-Evans, G. O.; Borgnakke, W. S.; Taylor, G. W.; Page, R. C.; Beck, J. D.; Genco, R. J. Update on prevalence of periodontitis in adults in the United States: NHANES 2009 to 2012. *J. Periodontol.* 2015, 86, 611-622. DOI: 10.1902/jop.2015.140520.
2. Eke, P. I.; Thornton-Evans, G. O.; Wei, L.; Borgnakke, W. S.; Dye, B. A.; Genco, R. J. Periodontitis in US adults: National health and nutrition examination survey 2009-2014. *J. Am. Dent. Assoc.* 2018, 149, 576-588 e6. 10.1016/j.adaj.2018.04.023.
3. Kholy, K. E.; Genco, R. J.; Van Dyke, T. E. Oral infections and cardiovascular disease. *Trends Endocrinol. Metab.* 2015, 26, 315-321. DOI: 10.1016/j.tem.2015.03.001.
4. Cullinan, M. P.; Ford, P. J.; Seymour, G. J. Periodontal disease and systemic health: current status. *Aust. Dent. J.* 2009, 54 Suppl 1, S62-69. DOI: 10.1111/j.1834-7819.2009.01144.x.
5. Routsias, J. G.; Goules, J. D.; Goules, A.; Charalampakis, G.; Pikazis, D. Autopathogenic correlation of periodontitis and rheumatoid arthritis. *Rheumatology (Oxford)* 2011, 50, 1189-1193. DOI: 10.1093/rheumatology/ker090.
6. Kolenbrander, P. E.; Palmer, R. J., Jr.; Periasamy, S.; Jakubovics, N. S. Oral multispecies biofilm development and the key role of cell-cell distance. *Nat. Rev. Microbiol.* 2010, 8, 471-480. DOI: 10.1038/nrmicro2381.
7. How, K. Y.; Song, K. P.; Chan, K. G. *Porphyromonas gingivalis*: An overview of periodontopathic pathogen below the gum line. *Front. Microbiol.* 2016, 7, 53. DOI: 10.3389/fmicb.2016.00053.
8. Lamont, R. J.; Jenkinson, H. F. Life below the gum line: pathogenic mechanisms of *Porphyromonas gingivalis*. *Microbiol. Mol. Biol. Rev.* 1998, 62, 1244-1263.
9. Holt, S. C.; Kesavalu, L.; Walker, S.; Genco, C. A. Virulence factors of *Porphyromonas gingivalis*. *Periodontol. 2000* 1999, 20, 168-238. DOI: 10.1111/j.1600-0757.1999.tb00162.x.
10. Bostanci, N.; Belibasakis, G. N. *Porphyromonas gingivalis*: an invasive and evasive opportunistic oral pathogen. *FEMS Microbiol. Lett.* 2012, 333, 1-9. DOI: 10.1111/j.1574-6968.2012.02579.x.
11. Hajishengallis, G.; Liang, S.; Payne, M. A.; Hashim, A.; Jotwani, R.; Eskan, M. A.; McIntosh, M. L.; Alsam, A.; Kirkwood, K. L.; Lambris, J. D.; Darveau, R. P.; Curtis, M. A. Low-abundance biofilm species orchestrates inflammatory periodontal disease through the commensal microbiota and complement. *Cell Host Microbe* 2011, 10, 497-506. DOI: 10.1016/j.chom.2011.10.006.
12. Hajishengallis, G.; Darveau, R. P.; Curtis, M. A. The keystone-pathogen hypothesis. *Nat. Rev. Microbiol.* 2012, 10, 717-725. DOI: 10.1038/nrmicro2873.
13. Lamont, R. J.; Chan, A.; Belton, C. M.; Izutsu, K. T.; Vasel, D.; Weinberg, A. *Porphyromonas gingivalis* invasion of gingival epithelial cells. *Infect. Immun.* 1995, 63, 3878-3885.
14. Mombelli, A.; Samaranayake, L. P. Topical and systemic antibiotics in the management of periodontal diseases. *Int. Dent. J.* 2004, 54, 3-14.
15. Mombelli, A.; Almaghlouth, A.; Cionca, N.; Courvoisier, D. S.; Giannopoulou, C. Differential benefits of amoxicillin-metronidazole in different phases of periodontal therapy in a randomized controlled crossover clinical trial. *J. Periodontol.* 2015, 86, 367-375. DOI: 10.1902/jop.2014.140478.
16. Mombelli, A.; Cionca, N.; Almaghlouth, A.; Cherkaoui, A.; Schrenzel, J.; Giannopoulou, C. Effect of periodontal therapy with amoxicillin-metronidazole on pharyngeal carriage of penicillin- and erythromycin-resistant *Viridans* streptococci. *J. Periodontol.* 2016, 87, 539-547. DOI: 10.1902/jop.2015.150494.
17. Haffajee, A. D.; Socransky, S. S.; Gunsolley, J. C. Systemic anti-infective periodontal therapy. A systematic review. *Ann. Periodontol.* 2003, 8, 115-181. DOI: 10.1902/annals.2003.8.1.115.
18. Ellen, R. P.; McCulloch, C. A. Evidence versus empiricism: rational use of systemic antimicrobial agents for treatment of periodontitis. *Periodontol. 2000* 1996, 10, 29-44. DOI: 10.1111/j.1600-0757.1996.tb00067.x.
19. Rams, T. E.; Degener, J. E.; van Winkelhoff, A. J. Antibiotic resistance in human chronic periodontitis microbiota. *J. Periodontol.* 2014, 85, 160-169. DOI: 10.1902/jop.2013.130142.
20. Ashburn, T. T.; Thor, K. B. Drug repositioning: identifying and developing new uses for existing drugs. *Nat. Rev. Drug Discov.* 2004, 3, 673-683. DOI: 10.1038/nrd1468.
21. Chong, C. R.; Sullivan, D. J., Jr. New uses for old drugs. *Nature* 2007, 448, 645-646. DOI: 10.1038/448645a.
22. Rangel-Vega, A.; Bernstein, L. R.; Mandujano-Tinoco, E. A.; Garcia-Contreras, S. J.; Garcia-Contreras, R. Drug repurposing as an alternative for the treatment of recalcitrant bacterial infections. *Front. Microbiol.* 2015, 6, 282. DOI: 10.3389/fmicb.2015.00282.
23. Antunes, L. C.; Imperi, F.; Minandri, F.; Visca, P. In vitro and in vivo antimicrobial activities of gallium nitrate against multidrug-resistant *Acinetobacter baumannii*. *Antimicrob. Agents Chemother.* 2012, 56, 5961-5970. DOI: 10.1128/AAC.01519-12.
24. Attila, C.; Ueda, A.; Wood, T. K. 5-Fluorouracil reduces biofilm formation in *Escherichia coli* K-12 through global regulator AriR as an antivirulence compound. *Appl. Microbiol. Biotechnol.* 2009, 82, 525-533. DOI: 10.1007/s00253-009-1860-8.
25. Carlson-Banning, K. M.; Chou, A.; Liu, Z.; Hamill, R. J.; Song, Y.; Zechiedrich, L. Toward repurposing ciclopirox as an antibiotic against drug-resistant *Acinetobacter baumannii*, *Escherichia coli*, and *Klebsiella pneumoniae*. *PLoS One* 2013, 8, e69646. DOI: 10.1371/journal.pone.0069646.
26. Imperi, F.; Massai, F.; Ramachandran Pillai, C.; Longo, F.; Zennaro, E.; Rampioni, G.; Visca, P.; Leoni, L. New life for an old drug: the anthelmintic drug niclosamide inhibits *Pseudomonas aeruginosa* quorum sensing. *Antimicrob. Agents Chemother.* 2013, 57, 996-1005. DOI: 10.1128/AAC.01952-12.
27. Imperi, F.; Massai, F.; Facchini, M.; Frangipani, E.; Visaggio, D.; Leoni, L.; Bragonzi, A.; Visca, P. Repurposing the antimycotic drug flucytosine for suppression of *Pseudomonas aeruginosa* pathogenicity. *Proc. Natl. Acad. Sci., U.S.A.* 2013, 110, 7458-7463. DOI: 10.1073/pnas.1222706110.
28. Scow, D. T.; Luttermoser, G. K.; Dickerson, K. S. Leukotriene inhibitors in the treatment of allergy and asthma. *Am. Fam. Physician* 2007, 75, 65-70.
29. Schierle, S.; Flauaus, C.; Heitel, P.; Willems, S.; Schmidt, J.; Kaiser, A.; Weizel, L.; Goebel, T.; Kahnt, A. S.; Geisslinger, G.; Steinhilber, D.; Wurglics, M.; Rovati, G. E.; Schmidtko, A.; Proschak, E.; Merk, D. Boosting anti-inflammatory potency of zafirlukast by designed polypharmacology. *J. Med. Chem.* 2018, 61, 5758-5764. DOI: 10.1021/acs.jmedchem.8b00458.
30. Martinez, A. A.; Espinosa, B. A.; Adamek, R. N.; Thomas, B. A.; Chau, J.; Gonzalez, E.; Keppetipola, N.; Salzameda, N. T. Breathing new life into West Nile virus therapeutics; discovery and study of zafirlukast as an NS2B-NS3 protease inhibitor. *Eur. J. Med. Chem.* 2018, 157, 1202-1213. DOI: 10.1016/j.ejmech.2018.08.077.
31. Pinault, L.; Han, J. S.; Kang, C. M.; Franco, J.; Ronning, D. R. Zafirlukast inhibits complexation of Lsr2 with DNA and growth of *Mycobacterium tuberculosis*. *Antimicrob. Agents Chemother.* 2013, 57, 2134-2140. DOI: 10.1128/AAC.02407-12.
32. Gerits, E.; Van der Massen, I.; Vandamme, K.; De Cremer, K.; De Brucker, K.; Thevissen, K.; Cammue, B. P. A.; Beullens, S.; Fauvart, M.; Verstraeten, N.; Michiels, J.; Roberts, M. In vitro activity of the antiasthmatic drug zafirlukast against the oral pathogens *Porphyromonas gingivalis* and *Streptococcus mutans*. *FEMS Microbiol. Lett.* 2017, 364, DOI: 10.1093/femsle/fnx005.
33. Ancell, C. L.; Derrick, I.; Moseley, J. D.; Stott, J. A. Investigation into the acidification process of zafirlukast nitroacid leads to a surprising improvement in product quality. 2004, *Org. Proc. Res. Dev.*, 808-813. DOI: 10.1021/op049911+.
34. Srinivas, K.; Srinivasan, N.; Krishna, M. R.; Reddy, A. R.; Arunagiri, M.; Lalitha, R.; Reddy, K. S. R.; Reddy, P. P.; Kumar, M. K.; Reddy, M. S. A novel and efficient route to zafirlukast. Org. Proc. Res. Dev. 2004, 8, 952-954. DOI: 10.1021/op049869i.
35. Goverdhan, G.; Reddy, A. R.; Sampath, A.; Srinivas, K.; Himabindu, V.; Reddy, G. M. An improved and scalable process for zafirlukast: An asthma drug. *Org. Proc. Res. Dev.* 2009, 13, 67-72. DOI: 10.1021/op800137b.
36. Matassa, V. G.; Maduskuie, T. P., Jr.; Shapiro, H. S.; Hesp, B.; Snyder, D. W.; Aharony, D.; Krell, R. D.; Keith, R. A. Evolution of a series of peptidoleukotriene antagonists: synthesis and structure/activity relationships of 1,3, 5-substituted indoles and indazoles. *J Med. Chem.* 1990, 33, 1781-1790. DOI: 10.1021/jm00168a037.
37. Jiang, X.; Tiwari, A.; Thompson, M.; Chen, Z.; Cleary, T. P.; Lee, T. B. K. A practical method for the N-methylation of indoles using dimethyl carbonate. *Org. Proc. Res. Dev.* 2001, 5, 604-608. DOI: 10.1021/op0102215.
38. Goverdhan, G.; Reddy, A. R.; Himabindu, V.; Reddy, G. M. Concise and alternative synthesis of zafirlukast, an anti-asthma drug. *Synth. Commun.* 2013, 43, 498-504. DOI: 10.1080/00397911.2011.603875.
39. Paladugu, S.; Mainkar, P. S.; Chandrasekhar, S. Synthesis of asthma drug zafirlukast (accolate) using intramolecular oxidative coupling via sp3 C—H bond activation. *ACS Omega* 2018, 3, 4289-4294. DOI: 10.1021/acsomega.8b00476.
40. Babich, H.; Zuckerbraun, H. L.; Barber, I. B.; Babich, S. B.; Borenfreund, E. Cytotoxicity of sanguinarine chloride to cultured human cells from oral tissue. *Pharmacol. Toxicol.* 1996, 78, 397-403. DOI: 10.1111/j.1600-0773.1996.tb00225.x.
41. Russo, F. B.; Pignatari, G. C.; Fernandes, I. R.; Dias, J. L.; Beltrao-Braga, P. C. Epithelial cells from oral mucosa: How to cultivate them? *Cytotechnology* 2016, 68, 2105-2114. DOI: 10.1007/s10616-016-9950-9.
42. Elmore, E.; Luc, T. T.; Steele, V. E.; Kelloff, G. J.; Redpath, J. L. The human epithelial cell cytotoxicity assay for determining tissue specific toxicity. *Methods Cell Sci.* 2000, 22, 17-24. DOI: 10.1023/A: 1024453300493.
43. Chen, F.; Wu, T.; Cheng, X. Cytotoxic effects of denture adhesives on primary human oral keratinocytes, fibroblasts and permanent L929 cell lines. *Gerodontology* 2014, 31, 4-10. DOI: 10.1111/j.1741-2358.2012.00681.x.
44. Dickson, M. A.; Hahn, W. C.; Ino, Y.; Ronfard, V.; Wu, J. Y.; Weinberg, R. A.; Louis, D. N.; Li, F. P.; Rheinwald, J. G. Human keratinocytes that express hTERT and also bypass a p16(INK4a)-enforced mechanism that limits life span become immortal yet retain normal growth and differentiation characteristics. *Mol. Cell. Biol.* 2000, 20, 1436-1447. DOI: 10.1128/MCB.20.4.1436-1447.2000.
45. Tolnai, G. L.; Ganss, S.; Brand, J. P.; Waser, J. C2-selective direct alkynylation of indoles. Org. Lett. 2013, 15, 112-115. DOI: 10.1021/ol3031389.
46. 4. Gonzalez, O. A.; Escamilla, C.; Danaher, R. J.; Dai, J.; Ebersole, J. L.; Mumper, R. J.; Miller, C. S. Antibacterial effects of blackberry extract target periodontopathogens. *J. Periodontal. Res.* 2013, 48, 80-86. DOI: 10.1111/j.1600-0765.2012.01506.x.

It will be understood that various details of the presently disclosed subject matter can be changed without departing from the scope of the subject matter disclosed herein.

Furthermore, the foregoing description is for the purpose of illustration only, and not for the purpose of limitation.

What is claimed is:

1. A compound having the formula (I) or a pharmaceutically acceptable salt thereof:

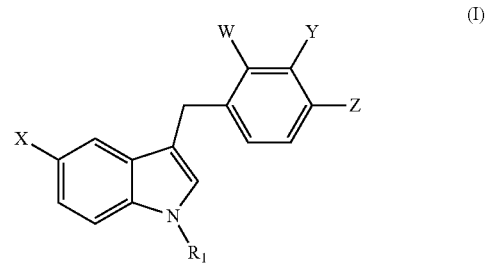

wherein,

R$_1$ is H or lower alkyl;

W, Y, and Z are independently selected from H,

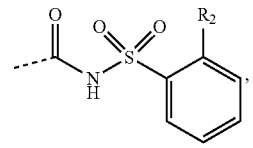

and OR$_3$, so long as only one of W, Y, and Z is

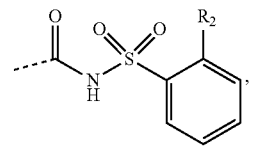

and R$_2$ and R$_3$ are each independently selected from H or lower alkyl; and

X is H, NO$_2$, N(R$_4$)$_2$, or SO$_2$R$_5$ where R$_4$ is H or lower alkyl, and R$_5$ is H or lower alkyl;

provided that, where R$_1$ is lower alkyl, W is OR$_3$, R$_3$ is lower alkyl, Y is H, and Z is

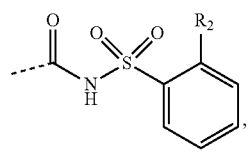

(i) when $R_2$ is H; then X is H, $NO_2$, $N(R_4)_2$, or $SO_2R_5$ where $R_4$ is H or lower alkyl, and $R_5$ is H or lower alkyl; and (ii) when $R_2$ is lower alkyl; then X is $N(R_4)_2$ or $SO_2R_5$ where $R_4$ is lower alkyl, and $R_5$ is H or lower alkyl.

2. The compound of claim 1, selected from formulas (III, IV, or V) or a pharmaceutically acceptable salt thereof:

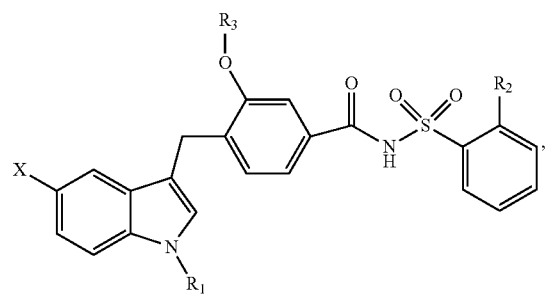

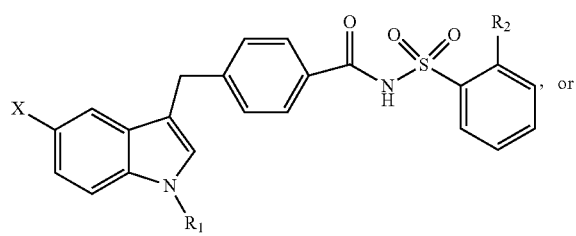

wherein $R_1$ is H or lower alkyl;

$R_2$ and $R_3$ are each independently selected from H or lower alkyl; and

X is H, $NO_2$, $N(R_4)_2$, or $SO_2R_5$ where $R_4$ is H or lower alkyl, and $R_5$ is H or lower alkyl.

3. The compound of claim 2, wherein $R_1$, $R_2$, and $R_3$ are each independently H or methyl; and X is H or $NO_2$.

4. The compound of claim 3, wherein $R_3$ is methyl.

5. The compound of claim 1, having the formula(V):

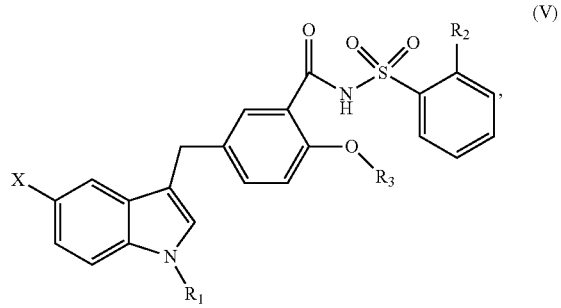

wherein $R_1$ and $R_2$ are each independently H or methyl; $R_3$ is methyl; and X is H or $NO_2$.

6. The compound of claim 1, selected from formulas (IV, VI, VIII, IX, X, XI, XII, XIII, XIV, XV, or XVI) or a pharmaceutically acceptable salt thereof:

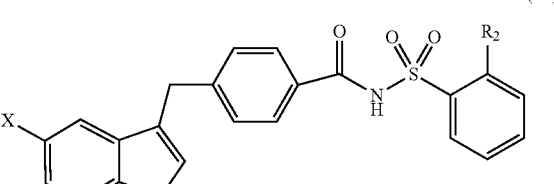

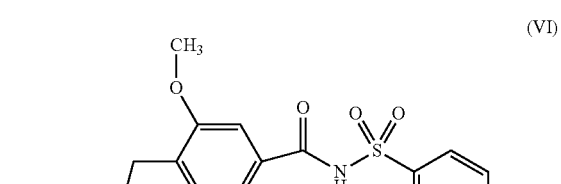

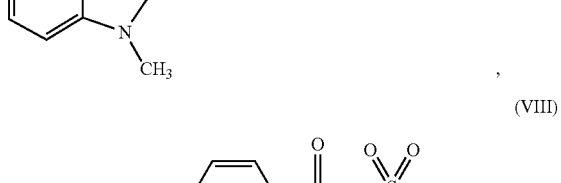

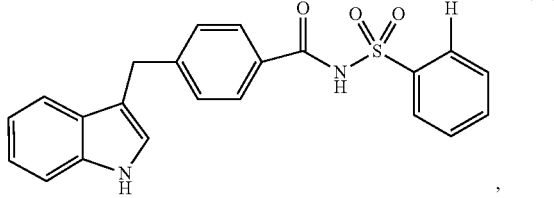

-continued

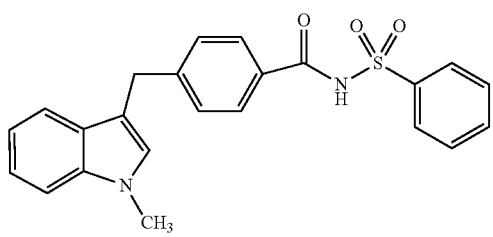
(X)

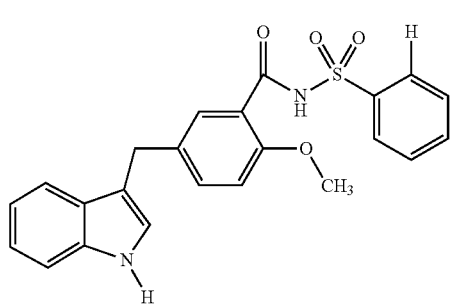
(XI)

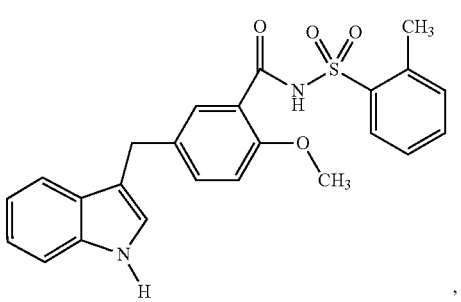
(XII)

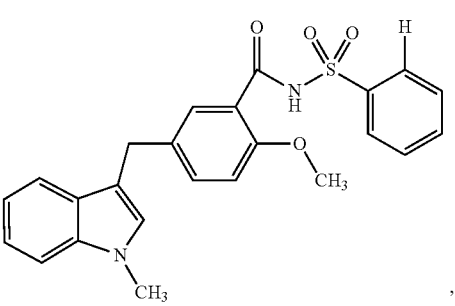
(XIII)

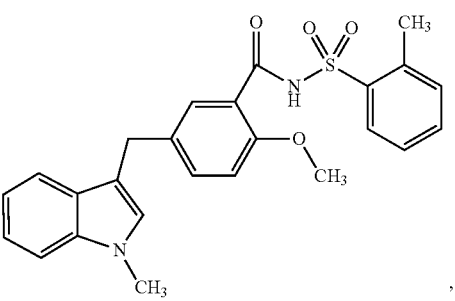
(XIV)

-continued

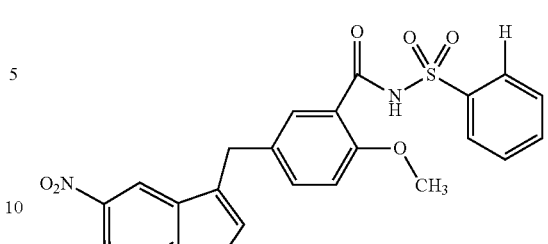
(XV)

, and

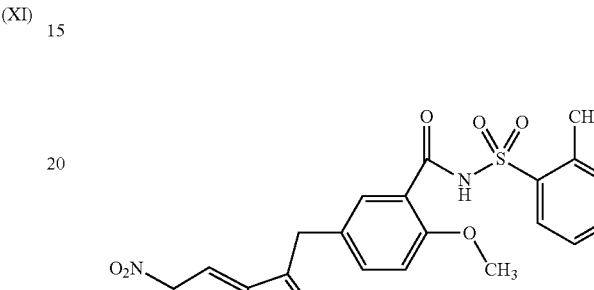
(XVI)

.

7. A pharmaceutical composition comprising the compound of claim 1, and a pharmaceutically-acceptable carrier.

8. A method of controlling a microbe, comprising:
contacting the microbe with an effective amount of the compound of claim 1.

9. The method of claim 8, wherein the microbe is *Porphyromonas* bacteria.

10. The method of claim 9, wherein the bacteria is *P. gingivalis*.

11. The method of claim 8, wherein the effective amount is from about 1 uM to about 100 uM.

12. A method of treating a microbial infection, comprising: administering to a subject in need thereof an effective amount of the compound of claim 1.

13. The method of claim 12, wherein the microbial infection is from *Porphyromonas* bacteria.

14. The method of claim 13, wherein the bacteria is *P. gingivalis*.

15. The method of claim 12, wherein the microbial infection caused by periodontal disease in the subject.

16. The method of claim 12, wherein the compound is administered prophylactically.

17. The method of claim 12, wherein the subject is identified as being at risk of infection.

18. The method of claim 12, wherein the effective amount is from about 1 uM to about 100 uM.

19. The method of claim 12, wherein the compound is selected from formulas (III, IV, or V) or a pharmaceutically acceptable salt thereof:

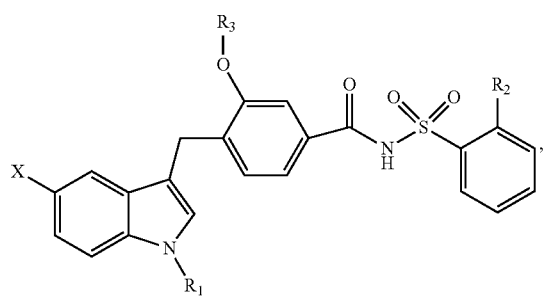
(III)
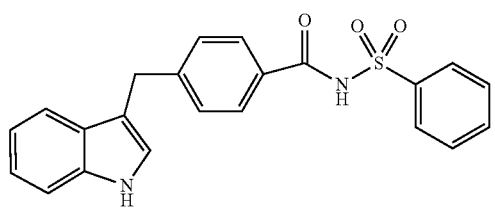
(VIII)
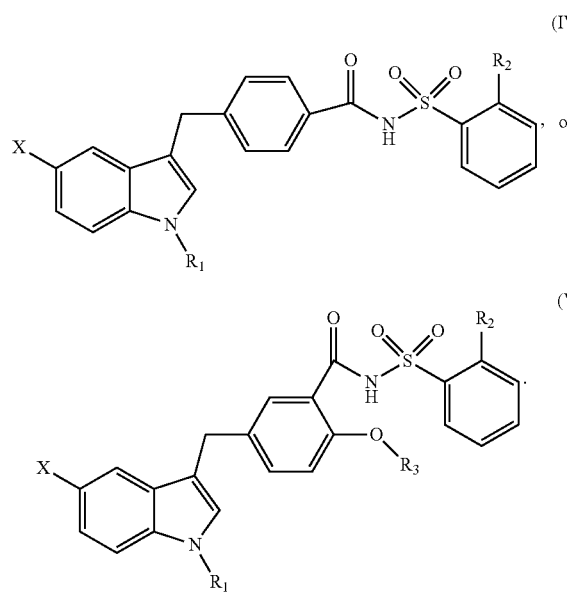
(IV), or
(V)
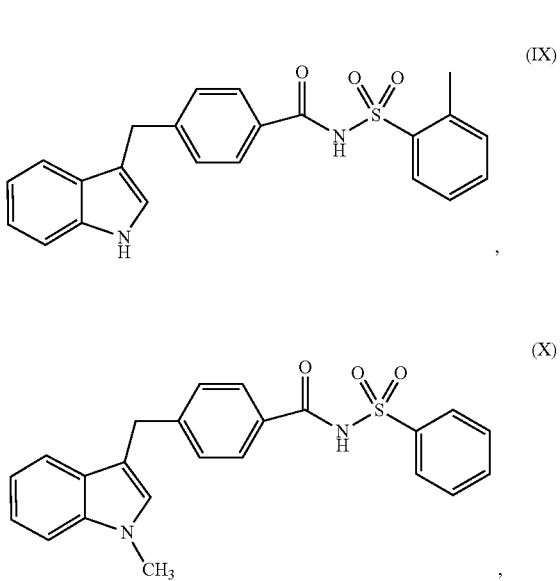
(IX)
(X)
20. The method of claim 12, wherein the compound is selected from formulas (IV, VI, VIII, IX, X, XI, XII, XIII, XIV, XV, XVI) or a pharmaceutically acceptable salt thereof:
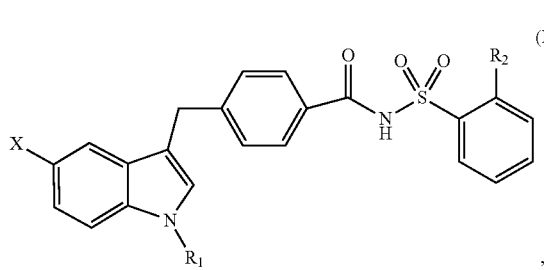
(IV)
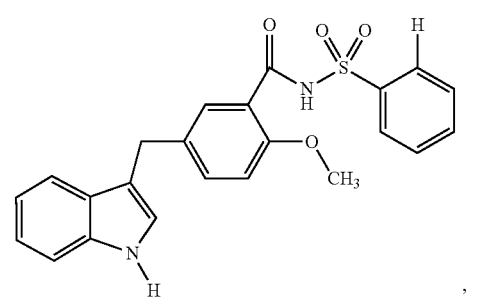
(XI)
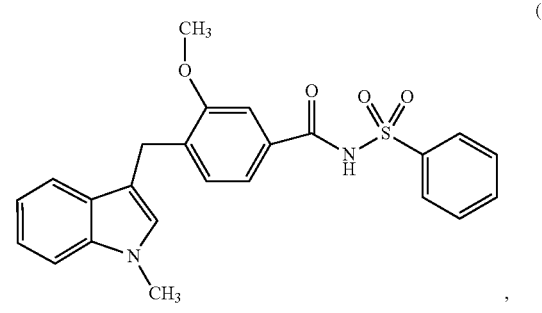
(VI)
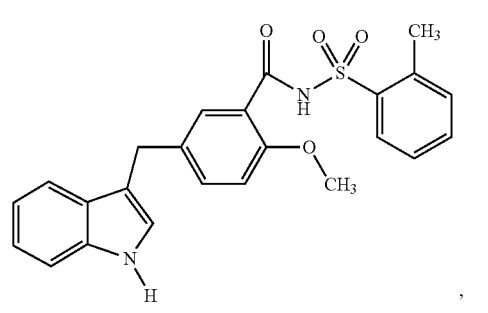
(XII)

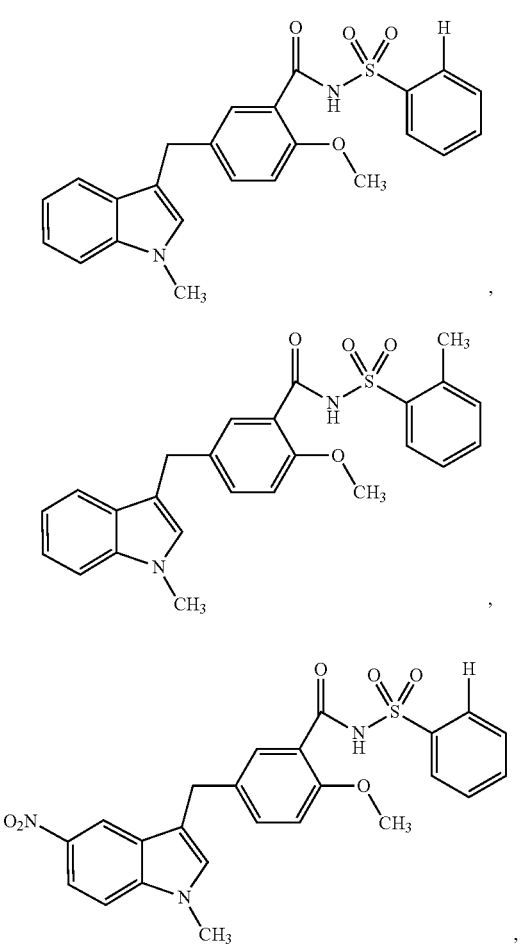
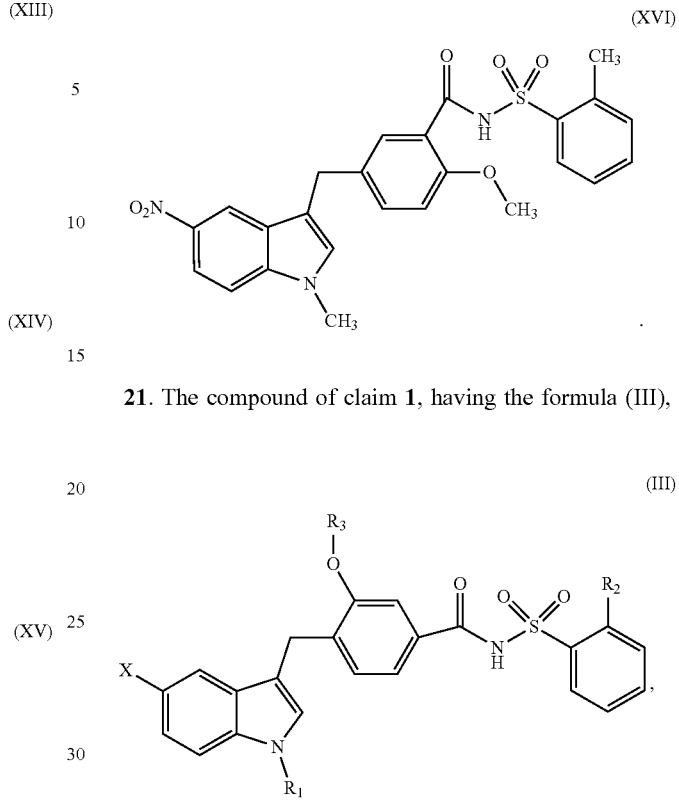
21. The compound of claim 1, having the formula (III),
wherein $R_1$ is H; $R_2$ is H or lower alkyl; $R_3$ is methyl; X is H, $NO_2$, $N(R_4)_2$, or $SO_2R_5$ where $R_4$ is H or lower alkyl, and $R_5$ is H or lower alkyl.
* * * * *